United States Patent [19]
Williamson, IV et al.

[11] Patent Number: 5,360,542
[45] Date of Patent: Nov. 1, 1994

[54] CENTRIFUGE WITH SEPARABLE BOWL AND SPOOL ELEMENTS PROVIDING ACCESS TO THE SEPARATION CHAMBER

[75] Inventors: Warren P. Williamson, IV, Cincinnati, Ohio; Richard I. Brown, Northbrook, Ill.

[73] Assignee: Baxter International Inc., Deerfield, Ill.

[21] Appl. No.: 147,015

[22] Filed: Nov. 2, 1993

Related U.S. Application Data

[63] Continuation of Ser. No. 814,403, Dec. 23, 1991, abandoned.

[51] Int. Cl.⁵ .................................................. B04B 7/08
[52] U.S. Cl. ................................ 210/232; 210/380.1; 210/512.1; 210/781; 422/72; 494/45
[58] Field of Search ............... 210/232, 380.1, 512.1, 210/781; 494/10, 16, 18, 21, 38, 41, 43, 45, 84; 422/72, 101

[56] References Cited

U.S. PATENT DOCUMENTS

| | | |
|---|---|---|
| Re. 29,738 | 8/1978 | Adams . |
| D. 255,935 | 7/1980 | Cullis et al. . |
| D. 255,936 | 7/1980 | Cullis et al. . |
| D. 258,909 | 4/1981 | Bergo et al. . |
| D. 314,824 | 2/1991 | Moon . |
| 3,244,363 | 4/1966 | Hein . |
| 3,347,454 | 10/1967 | Bellamy, Jr. et al. . |
| 3,489,145 | 1/1970 | Judson et al. . |
| 3,519,201 | 7/1970 | Eisel et al. . |
| 3,561,672 | 2/1971 | Schlutz et al. . |
| 3,655,123 | 4/1972 | Judson et al. . |
| 3,672,564 | 6/1972 | Schlutz et al. . |
| 3,737,096 | 6/1973 | Jones et al. . |
| 3,748,101 | 7/1973 | Jones et al. . |
| 3,786,919 | 1/1974 | Deringer . |
| 3,858,796 | 1/1975 | Unger et al. . |
| 3,957,197 | 5/1976 | Sartory et al. . |
| 3,987,961 | 10/1976 | Sinn et al. . |
| 4,007,871 | 2/1977 | Jones et al. . |
| 4,010,894 | 3/1977 | Kellogg et al. . |
| 4,056,224 | 11/1977 | Lolachi . |
| 4,094,461 | 6/1978 | Kellogg et al. . |
| 4,098,456 | 7/1978 | Bayham . |
| 4,108,353 | 8/1978 | Brown . |
| 4,109,852 | 8/1978 | Brown et al. . |
| 4,109,854 | 8/1978 | Brown . |
| 4,109,855 | 8/1978 | Brown et al. . |
| 4,111,356 | 9/1978 | Boggs et al. . |
| 4,113,173 | 9/1978 | Lolachi . |
| 4,114,802 | 9/1978 | Brown . |
| 4,120,448 | 10/1978 | Callis . |
| 4,120,449 | 10/1978 | Brown et al. . |
| 4,127,231 | 11/1978 | Khoja et al. . |
| 4,143,670 | 3/1979 | Ishimaru et al. . |
| 4,146,172 | 3/1979 | Cullis et al. . |

(List contined on next page.)

FOREIGN PATENT DOCUMENTS

| | | |
|---|---|---|
| 1303702 | 6/1992 | Canada . |
| 1304309 | 6/1992 | Canada . |
| WO91/15300 | 10/1991 | WIPO . |

OTHER PUBLICATIONS

"The Physics of Continuous Flow Centrifugal Cell Separation", Richard I. Brown, *Artificial Organs*, 13(1):4-30, Raven Press Ltd. 1989 Int. Soc. for Artificial Organs.

*Primary Examiner*—Robert A. Dawson
*Assistant Examiner*—David Reifsnyder
*Attorney, Agent, or Firm*—Bradford R. L. Price; Paul C. Flattery; Daniel D. Ryan

[57] ABSTRACT

A centrifuge provides simplify access to the processing chamber. In one arrangement, the processing chamber separates into a bowl and spool element to receive a disposable processing bag. In another arrangement, the processing chamber pivots between an operating position and an access position to provide improved access. The centrifuge also employs readily accessible holders for releasably retaining tubing that, in use, conveys fluid to and from the chamber. Though greatly accessible, the centrifuge operates without the need of complicated rotating seals and expensive disposable components.

18 Claims, 24 Drawing Sheets

U.S. PATENT DOCUMENTS

| | | | |
|---|---|---|---|
| 4,164,318 | 8/1979 | Boggs . | |
| 4,185,629 | 1/1980 | Cullis et al. . | |
| 4,187,979 | 2/1980 | Cullis et al. . | |
| 4,194,684 | 3/1980 | Boggs . | |
| 4,215,688 | 8/1980 | Terman et al. . | |
| 4,223,672 | 9/1980 | Terman et al. . | |
| 4,230,263 | 10/1980 | Westberg . | |
| 4,244,513 | 1/1981 | Fayer et al. . | |
| 4,261,507 | 4/1981 | Baumler | 494/45 |
| 4,266,717 | 5/1981 | Jennings et al. | 494/45 |
| 4,278,201 | 7/1981 | Cailliot . | |
| 4,278,202 | 7/1981 | Westberg . | |
| 4,283,004 | 8/1981 | Lamadrid . | |
| 4,283,276 | 8/1981 | Grant . | |
| 4,316,576 | 2/1982 | Cullis et al. . | |
| 4,330,080 | 5/1982 | Mathieu . | |
| 4,353,795 | 10/1982 | Romanauskas . | |
| 4,357,235 | 11/1982 | Dilks, Jr. . | |
| 4,379,452 | 4/1983 | DeVries . | |
| 4,386,730 | 6/1983 | Mulzet . | |
| 4,387,848 | 6/1983 | Kellogg et al. . | |
| 4,405,079 | 9/1983 | Schoendorfer . | |
| 4,419,089 | 12/1983 | Kolobow et al. . | |
| 4,425,112 | 1/1984 | Ito . | |
| 4,430,072 | 2/1984 | Kellogg et al. . | |
| 4,445,883 | 5/1984 | Schoendorfer . | |
| 4,446,014 | 5/1984 | Dilks, Jr. et al. . | |
| 4,446,015 | 5/1984 | Kirkland . | |
| 4,447,221 | 5/1984 | Mulzet . | |
| 4,448,679 | 5/1984 | Dilks, Jr. et al. . | |
| 4,530,691 | 7/1985 | Brown . | |
| 4,605,503 | 8/1986 | Bilstad et al. . | |
| 4,636,193 | 1/1987 | Cullis | 494/45 |
| 4,708,712 | 11/1987 | Mulzet . | |
| 4,710,161 | 12/1987 | Takabayashi et al. . | |
| 4,724,317 | 2/1988 | Brown et al. . | |
| 4,734,089 | 3/1988 | Cullis . | |
| 4,743,227 | 5/1988 | Takeuchi . | |
| 4,790,807 | 12/1988 | Neumann et al. . | |
| 4,834,890 | 5/1989 | Brown et al. . | |
| 4,850,995 | 7/1989 | Tie et al. . | |
| 4,851,126 | 7/1989 | Schoendorfer . | |
| 4,857,190 | 8/1989 | Wada et al. . | |
| 4,897,185 | 1/1990 | Schuyler et al. . | |
| 4,900,298 | 2/1990 | Langley . | |
| 4,934,995 | 6/1990 | Cullis . | |
| 4,936,820 | 6/1990 | Dennehey et al. . | |
| 4,968,295 | 11/1990 | Neumann . | |
| 4,975,186 | 12/1990 | Wada et al. . | |
| 4,990,132 | 2/1991 | Unger et al. . | |
| 5,006,103 | 4/1991 | Bacehowski et al. | 494/45 |
| 5,045,185 | 9/1991 | Ohnaka et al. . | |
| 5,067,938 | 11/1991 | Uchida et al. . | |
| 5,089,417 | 2/1992 | Wogoman . | |
| 5,104,526 | 4/1992 | Brown et al. . | |
| 5,135,667 | 8/1992 | Schoendorfer . | |
| 5,171,456 | 12/1992 | Hwang et al. . | |
| 5,194,145 | 3/1993 | Schoendorfer . | |
| 5,217,426 | 6/1993 | Bacehowski et al. . | |
| 5,217,427 | 6/1993 | Cullis . | |
| 5,234,608 | 8/1993 | Duff . | |

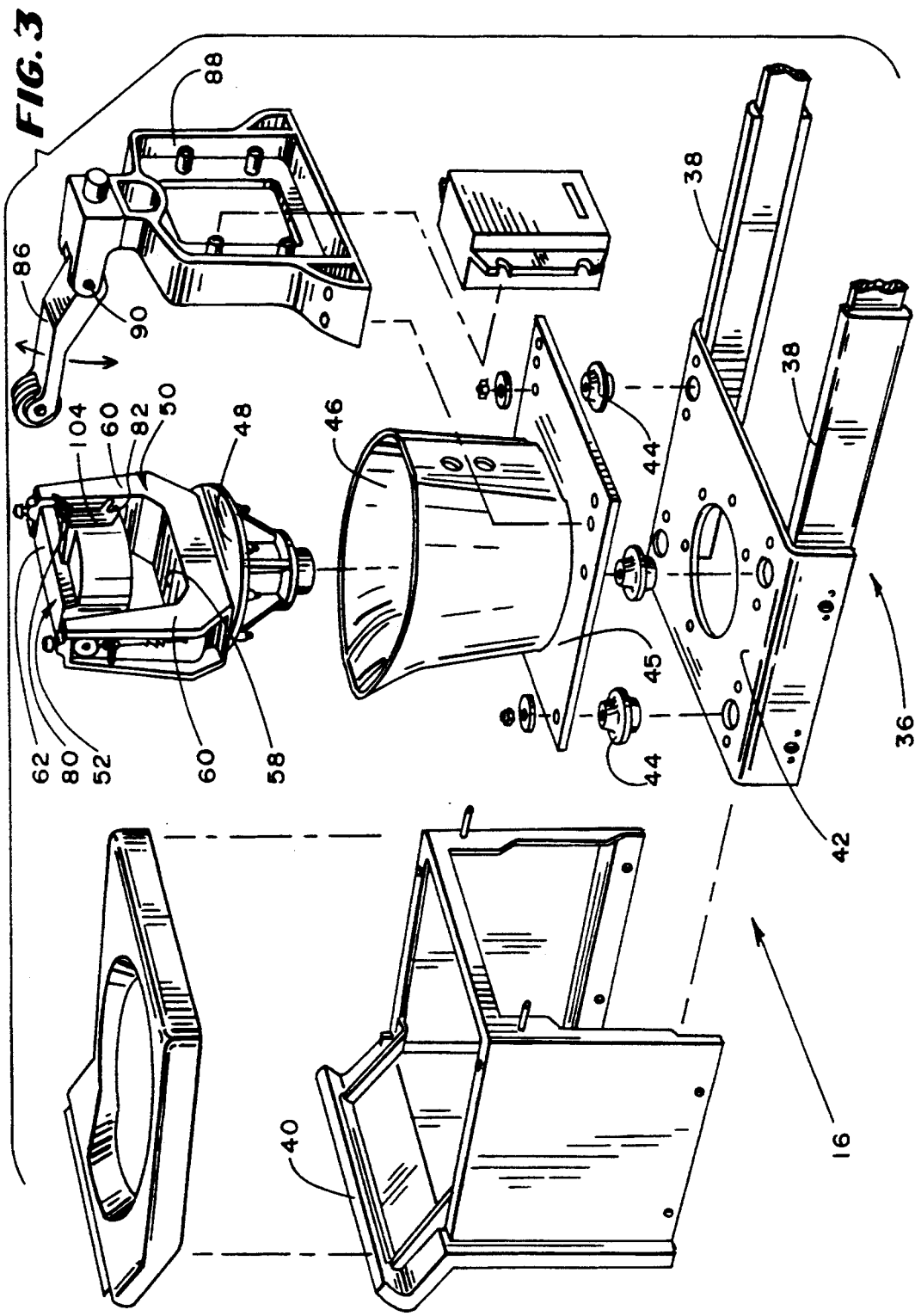

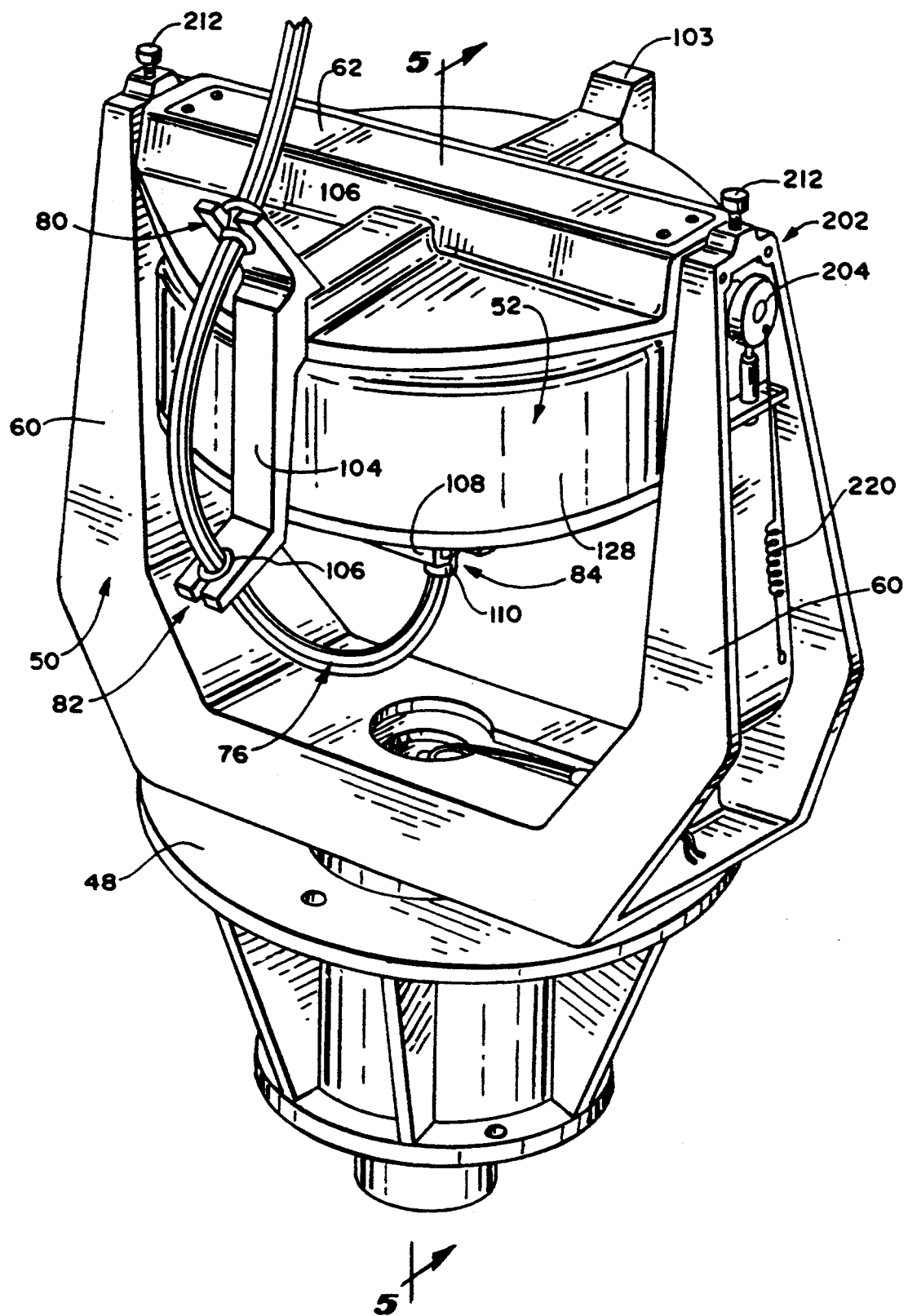

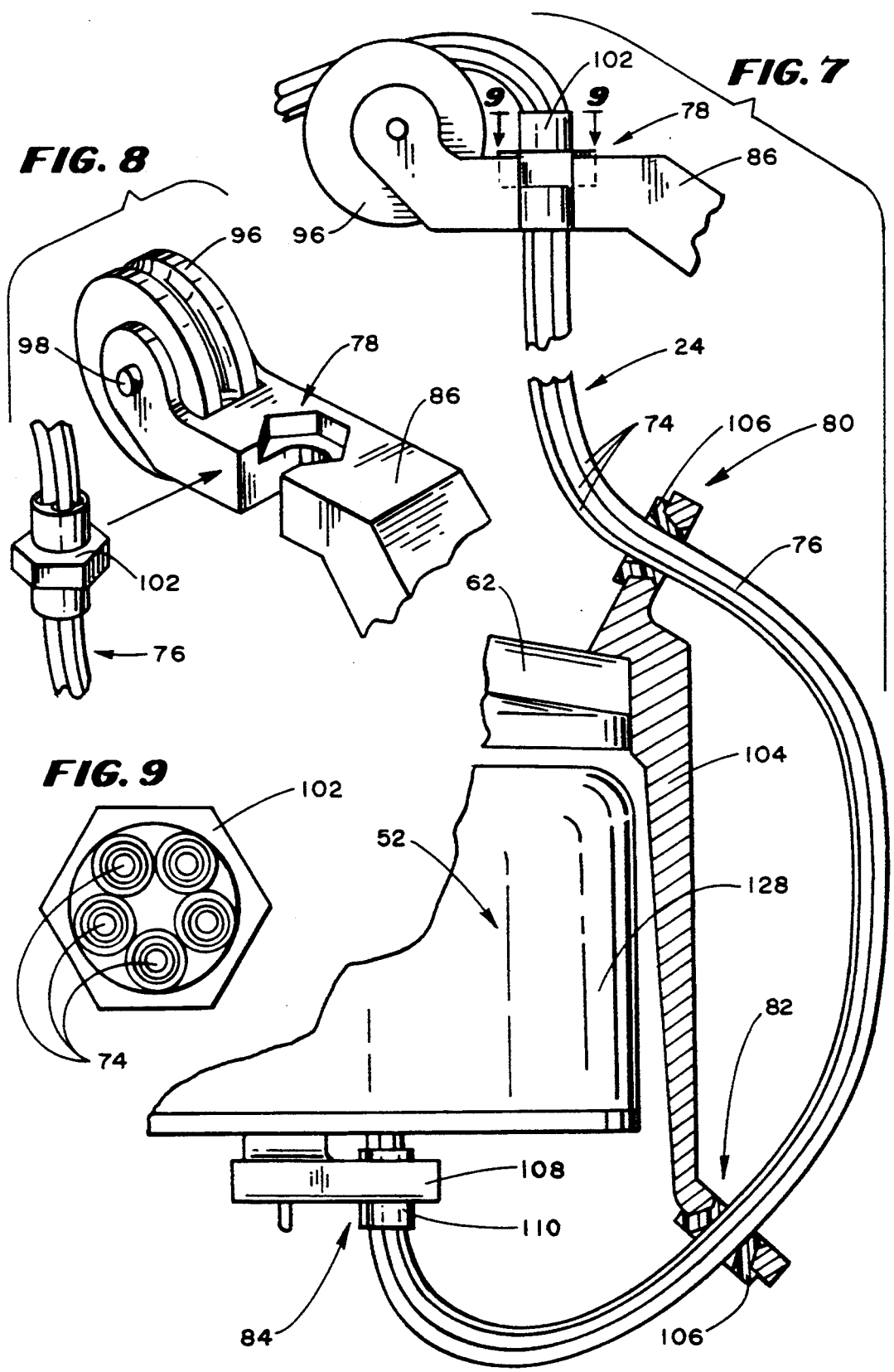

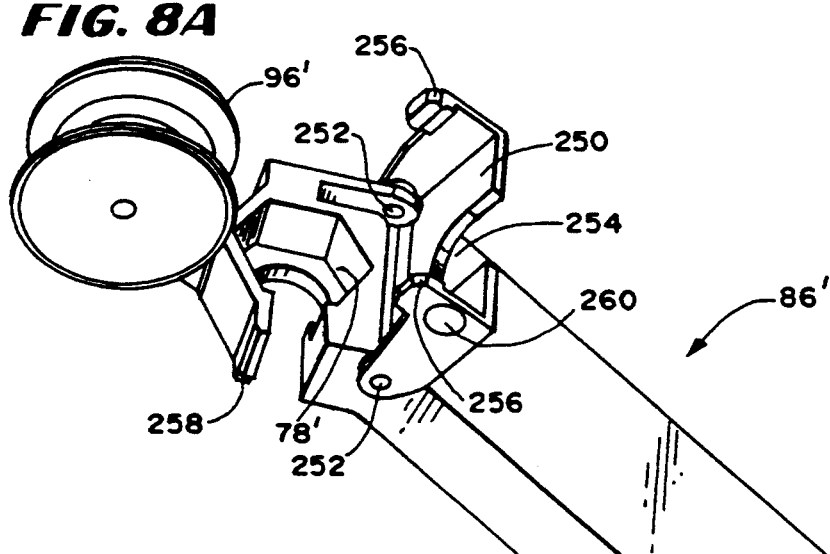
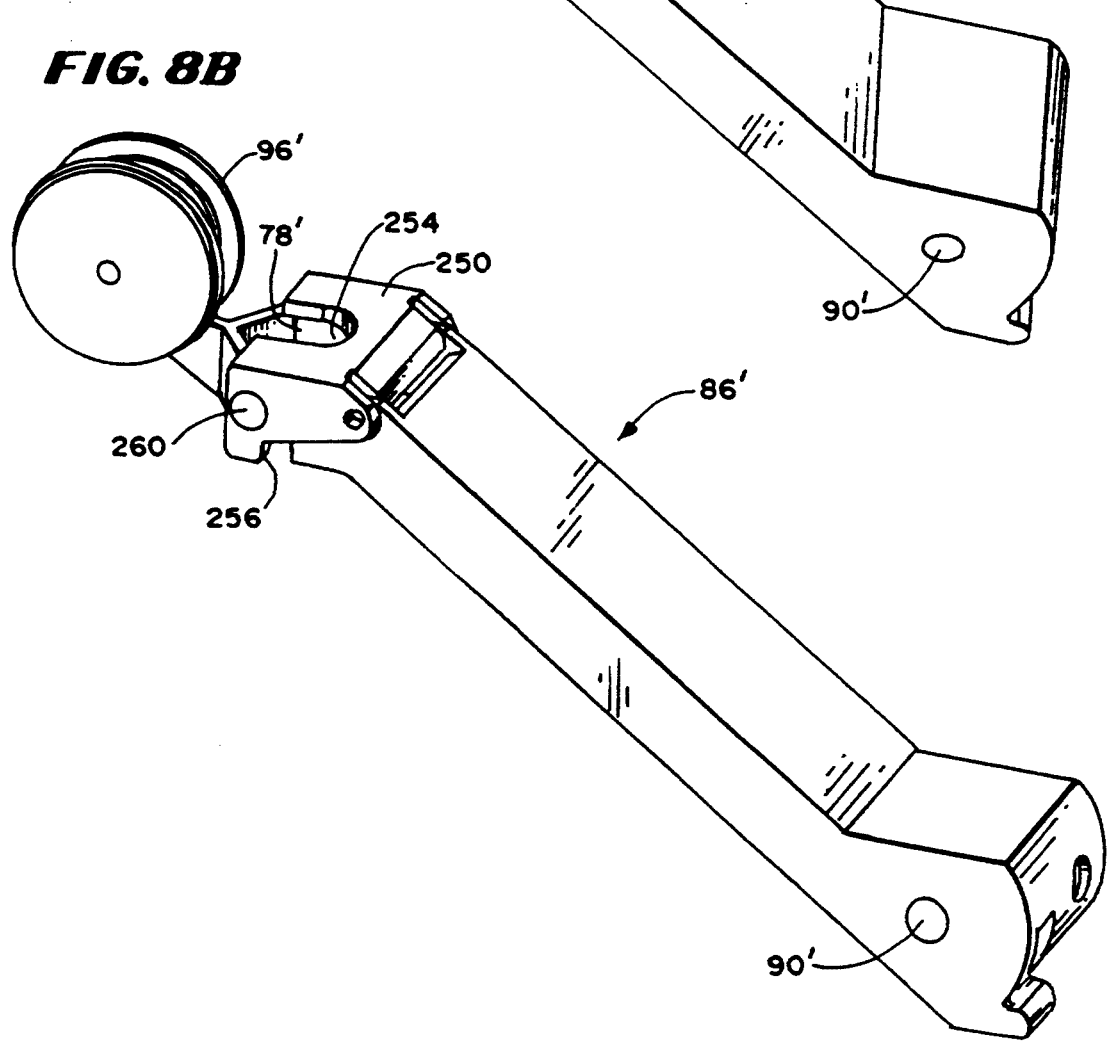

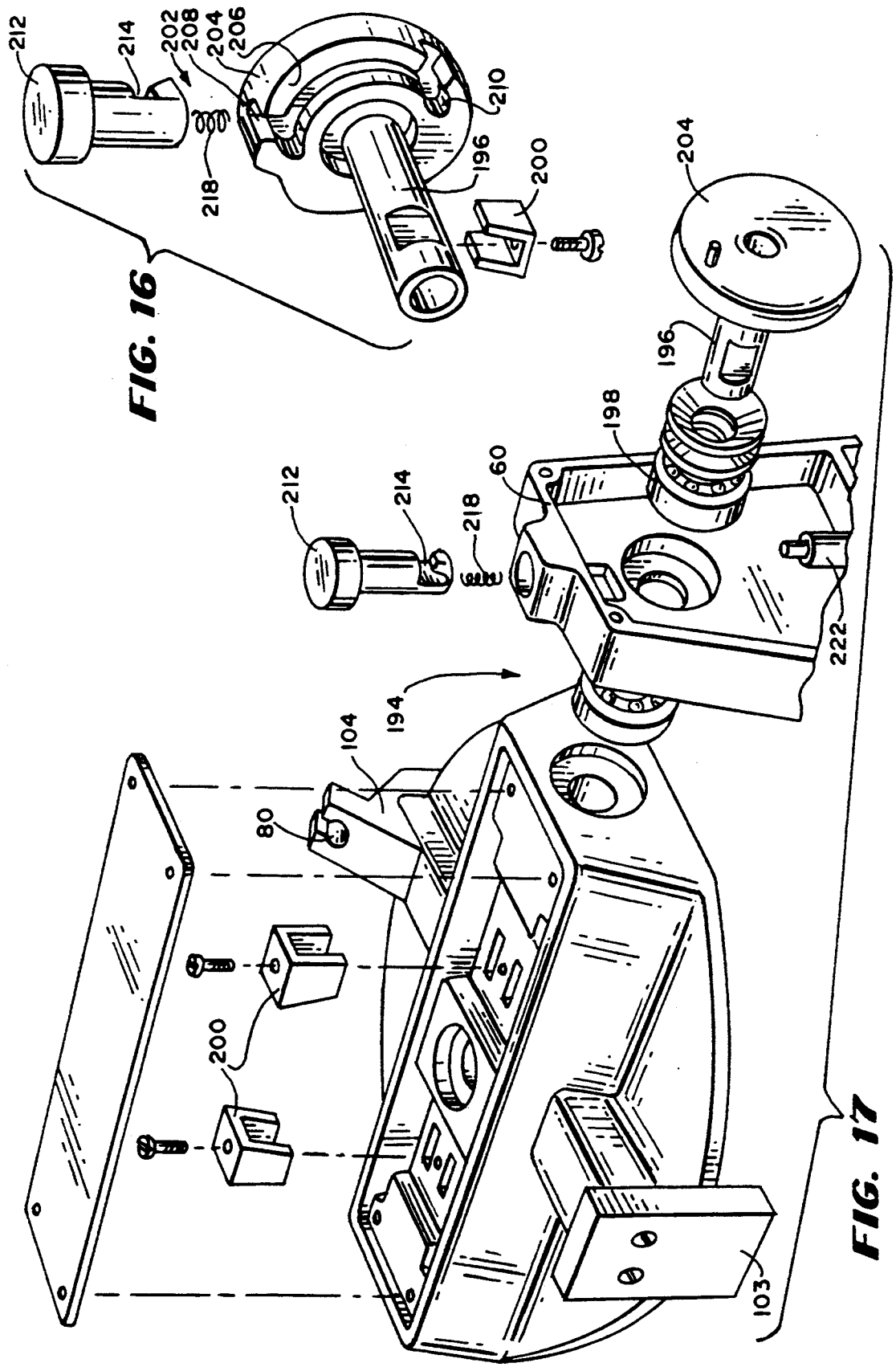

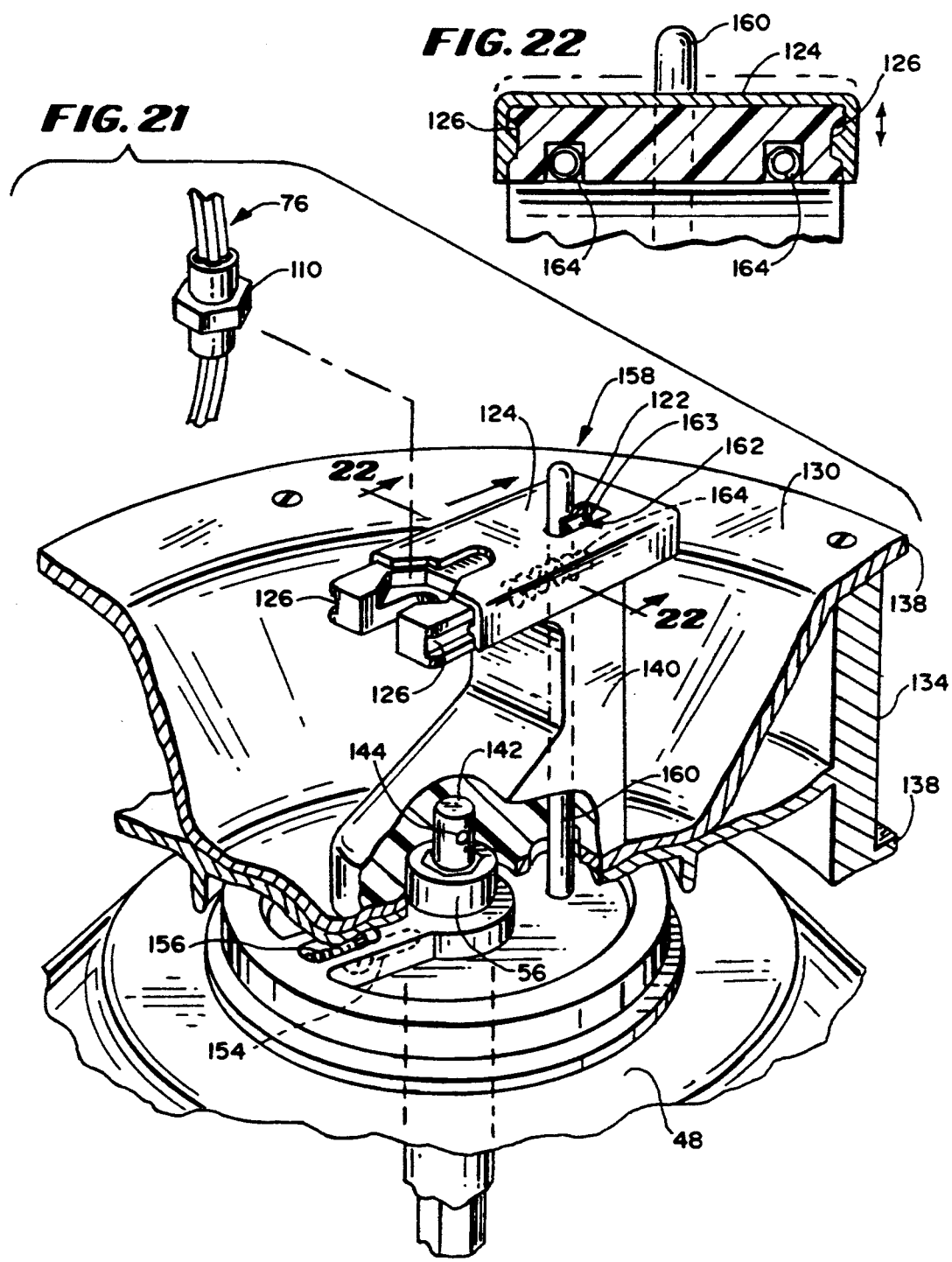

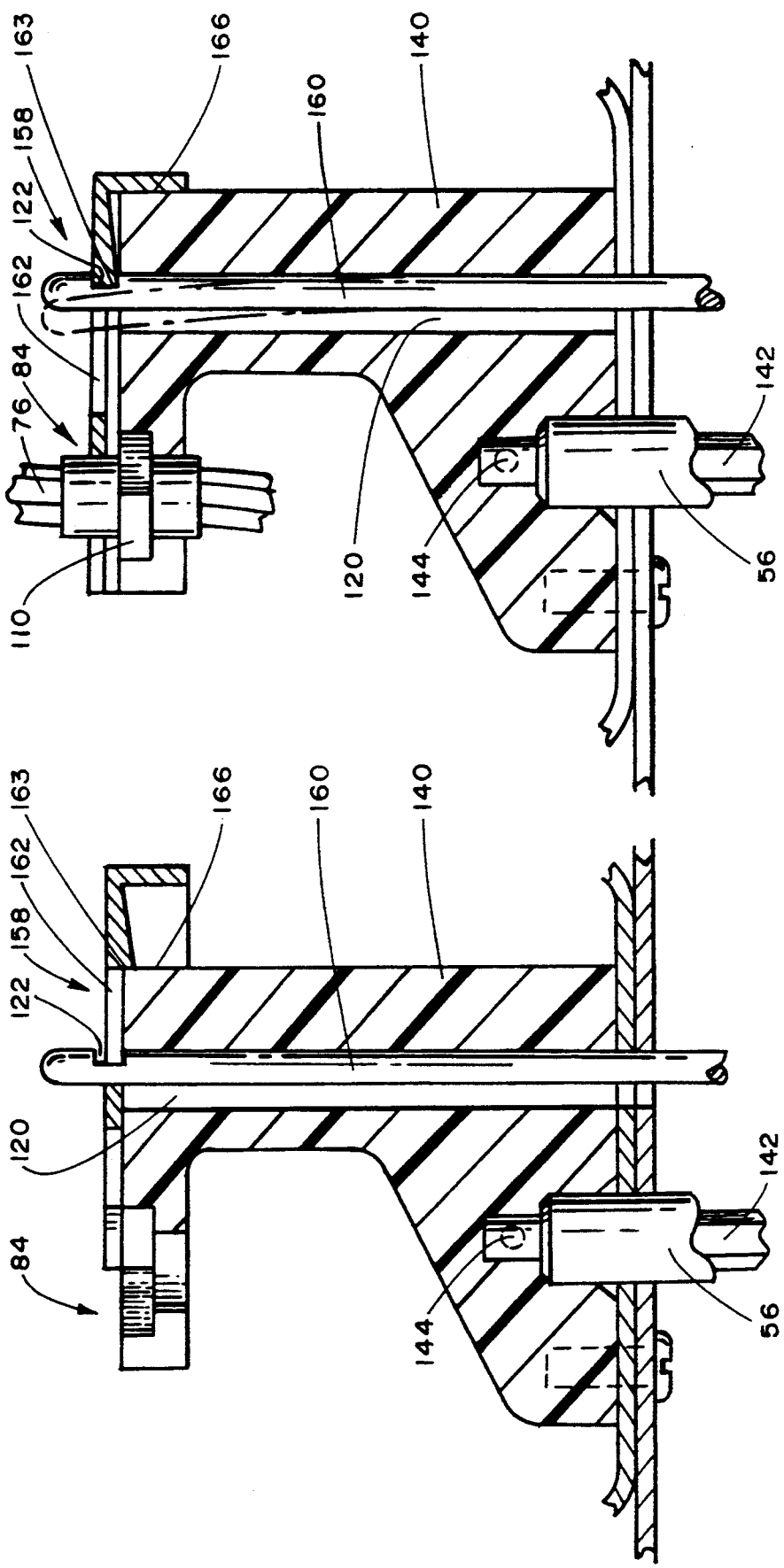

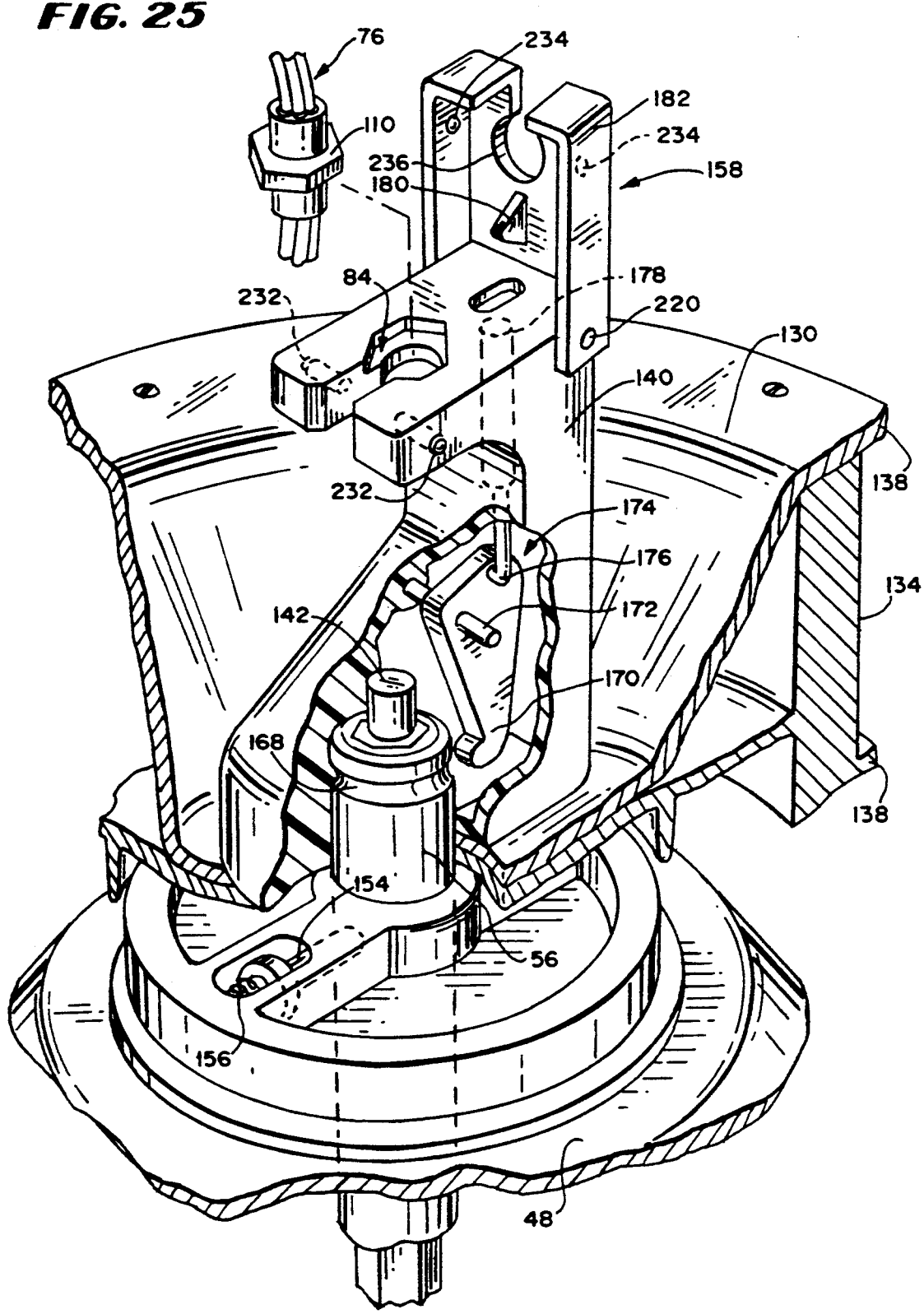

5,360,542

CENTRIFUGE WITH SEPARABLE BOWL AND SPOOL ELEMENTS PROVIDING ACCESS TO THE SEPARATION CHAMBER

This is a continuation of copending application(s) Ser. No. 07/814,403 filed Dec. 23, 1991, now abandoned.

FIELD OF THE INVENTION

The invention relates to centrifugal processing systems and apparatus.

BACKGROUND OF THE INVENTION

Today people routinely separate whole blood by centrifugation into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional centrifuges often do not permit easy access to the areas where the disposable systems reside during use. As a result, loading and unloading operations can be time consuming and tedious.

Disposable systems are often preformed into desired shapes to simplify the loading and unloading process. However, this approach is often counterproductive, as it increases the cost of the disposables.

SUMMARY OF THE INVENTION

The invention provides improved centrifugal processing systems that provide easy access to the rotating parts of the centrifuge for loading and unloading disposable processing components. The invention achieves this objective without complicating or increasing the cost of the disposable components. The invention allows relatively inexpensive and straight-forward disposable components to be used.

One aspect of the invention provides a processing chamber for a centrifuge. The chamber includes a bowl element having a wall enclosing an interior area and a spool element having an exterior surface. A mechanism joins the spool element and the bowl element.

The mechanism permits the spool and bowl elements to assume a mutually cooperating position. In this position, the spool element is enclosed within the interior area of the bowl element. The processing chamber is formed between the bowl wall and the exterior spool surface.

The mechanism also permits the spool and bowl to assume a mutually separated position. In this position, the spool element is at least partially out of the interior area of the bowl element to expose the exterior spool surface for access.

This arrangement forms an operational centrifugation chamber when necessary during processing operations. Still, the chamber can be opened up and made readily accessible to the user after the processing operations are over.

In a preferred arrangement, the spool element includes a mechanism that is exposed when the spool and bowl elements are in their mutually separated position, for receiving a processing element upon the spool exterior surface. The mechanism also retains the processing element within the processing chamber when the spool and bowl elements are moved to their mutually cooperating position during use.

The user can therefore quickly and easily handle the disposable processing elements that must be installed and then removed before and after each processing operation. This eliminates the need for expensive processing elements specially design to be fitted into tight and awkward quarters.

In a preferred embodiment, the mechanism that joins the spool and bowl elements allows the spool element to be detached from the bowl element for replacement by a second spool element. This interchangeability allows the user to configure the processing chamber by exchanging spool elements.

Other aspects of the invention further simplify access to the processing chamber of a centrifuge.

Another aspect of the invention provides a centrifuge having a processing chamber that rotates about a first axis. A mechanism pivots the processing chamber about a second axis between an operating position and an access position.

In the operating position, the processing chamber is oriented for centrifugal processing while being rotated about the first axis. In the access position, the processing chamber is oriented for access by the user.

The processing chamber is normally biased toward one of the operating and access positions. Still, the biasing mechanism allows movement of the processing chamber toward the other position in response to an external force other than gravity. In a preferred embodiment, the processing chamber is biased toward the access position. A mechanism locks the joined bowl and spool elements in the operating position, but will release the processing chamber for movement toward the access position in response to the biasing force.

In a preferred embodiment, the processing chamber includes separable spool and bowl elements, as already described.

Another aspect of the invention provides a holder that releasably receives a section of tubing that conveys fluid to or from the processing chamber. The holder assumes a first position holding the first section of tubing adjacent to the processing chamber for conducting fluid when the chamber is rotated in its operating position. The holder also assumes a second position free of the first section of tubing and spaced away from the processing chamber to allow user access to the processing chamber when in the access position.

In a preferred arrangement, the processing chamber includes a surface region where the chamber can be accessed. In this arrangement, when the processing chamber is in its operating position, the accessing region is generally oriented downward. When the processing chamber is in its access position, the accessing surface is generally oriented upward. The first holder is located above the processing chamber so that, when it is in its operating position, the accessing surface generally faces away. Likewise, when the processing chamber is in its access position, the accessing surface generally faces toward the first holder.

In a preferred arrangement, the centrifuge also includes a second holder on the accessing surface of the processing chamber. The second holder is operative for releasable receiving a second section of tubing that communicates with the first section of tubing for conveying fluid to or from the chamber. Being situated on the accessing surface, the second holder faces away from the first holder when the processing chamber is in its operating position and faces toward the first holder means when processing chamber is in its access position.

In a preferred embodiment, the centrifuge also includes a third holder that receives a third tubing section that lies between and communicates with the first and second tubing sections for conveying fluid to or from the chamber. The third holder orients the third tubing section axially of but spaced from the first axis.

In this preferred arrangement, the centrifuge includes a frame. The first holder is mounted to the frame. A first drive rotates the third holder at a first rate of rotation relative to the frame. A second drive rotates the processing chamber, and with it the second holder, relative to the frame while in the operating position at a second rate of rotation twice the first rate of rotation. This keeps the tubing from twisting during rotation, avoiding the use of rotating seals.

The features and advantages of the invention will become apparent from the following description, the drawings, and the claims.

BRIEF DESCRIPTION OF THE DRAWINGS

FIG. 3 is an exploded perspective view of the drawer and rotating components of the centrifuge assembly;

FIG. 4 is an enlarged perspective view of the rotating components of the centrifuge assembly shown in its suspended operating position;

FIG. 7 is an enlarged side elevation view of the umbilicus mounts associated with the centrifuge assembly;

FIG. 8 is an enlarged perspective view of the zero omega holder and associated upper umbilicus mount;

FIG. 8A is an enlarged perspective view of an alternative embodiment of the zero omega holder, with the associated latch member in its upraised position;

FIG. 8B is an enlarged perspective view of the alternative embodiment of the zero omega holder shown in FIG. 8A, with the associated latch member in its lowered position;

FIG. 9 is a top section view of the upper umbilicus block taken generally along line 9—9 in FIG. 7.

FIG. 16 is a perspective exploded view of the locking pin component of the swinging lock assembly that pivots the rotating components of the centrifuge assembly between operating and upraised positions;

FIG. 17 is a perspective exploded view of the entire swinging lock assembly that pivots the rotating components of the centrifuge assembly between its operating and upraised positions;

FIG. 21 is an enlarged and exploded perspective view, with portions broken away and in section, of a mechanism for moving and securing the centrifuge assembly in its open and closed positions, as well as clamping the umbilicus near the processing chamber;

FIG. 22 is a side section view, taken generally along line 22—22 in FIG. 21, of the latch member associated with the mechanism shown in FIG. 21;

FIGS. 23 and 24 are side section views showing the operation of the latch member associated with the mechanism shown in FIG. 21;

FIG. 25 is an enlarged and exploded perspective view, with portions broken away and in section, of an alternative mechanism for moving and securing the centrifuge assembly in its open and closed positions, as well as clamping the umbilicus near the processing chamber;

DESCRIPTION OF THE PREFERRED EMBODIMENTS

Figure 2:
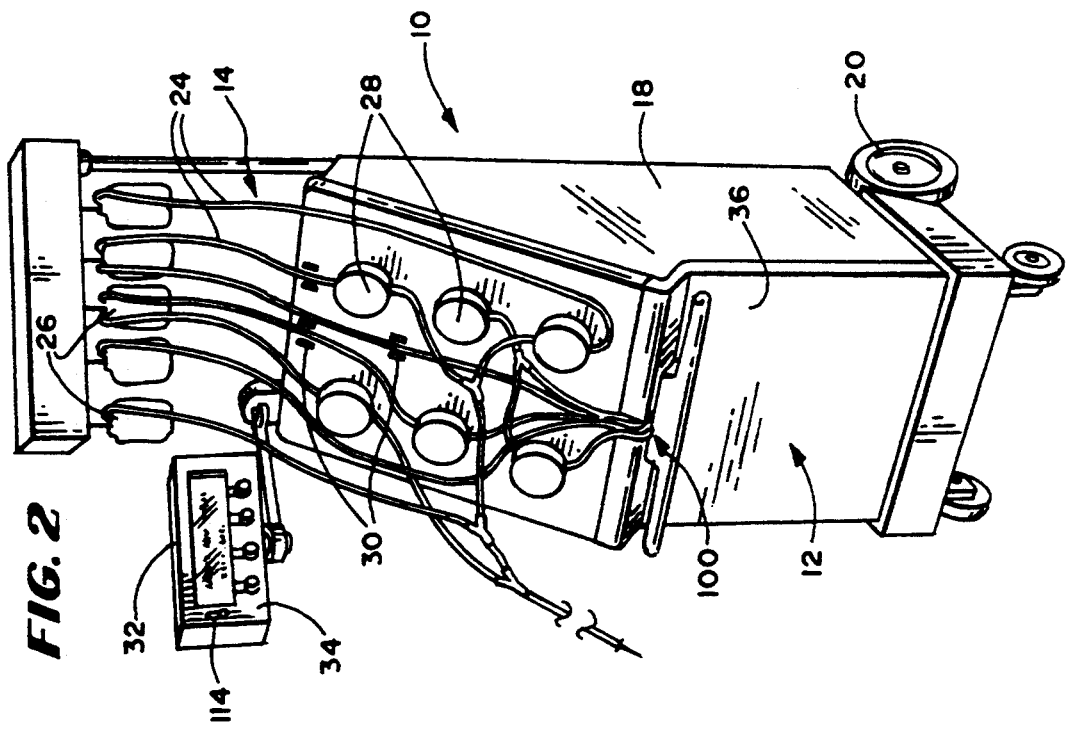
FIG. 2 is a front perspective view of the processing system shown in FIG. 1, with the drawer closed as it would be during normal processing operations.
Figure 1:
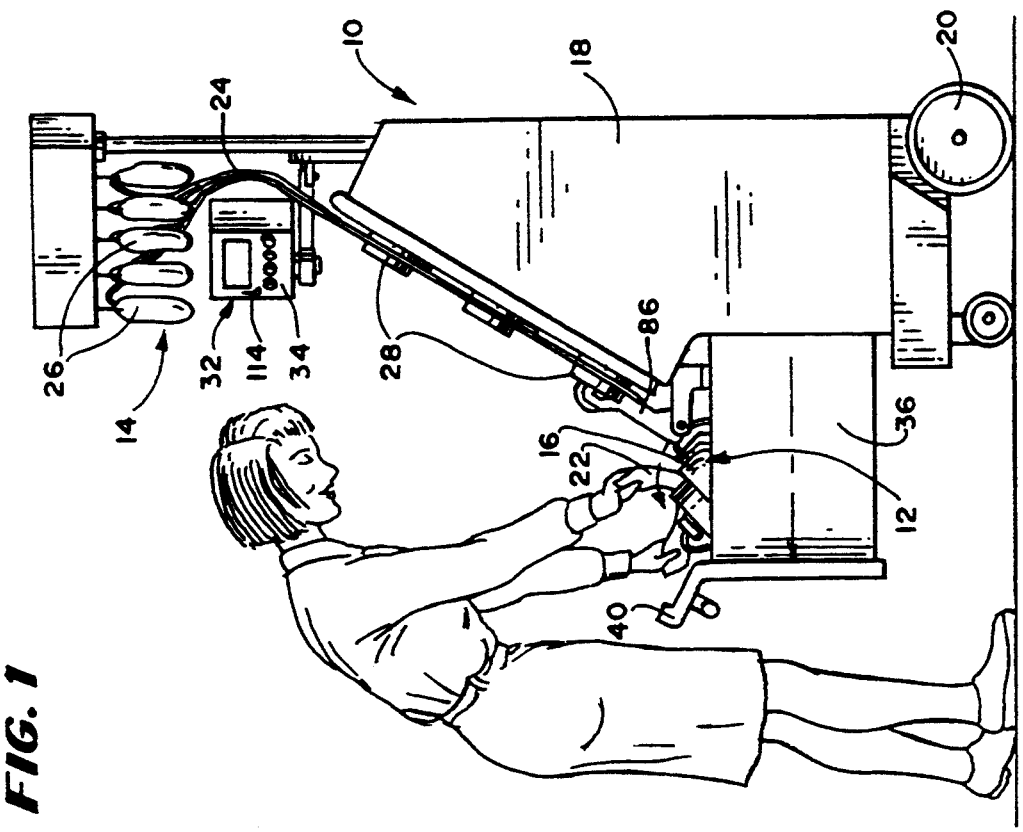
FIG. 1 is a side elevation view of a processing system that embodies the features of the invention, with the drawer carrying the rotating components of the centrifuge assembly shown in its open position for loading the associated fluid processing chamber.

FIGS. 1 and 2 show a centrifugal processing system 10 that embodies the features of the invention. The system 10 can be used for processing various fluids. The system 10 is particularly well suited for processing whole blood and other suspensions of cellular materials that are subject to trauma. Accordingly, the illustrated embodiment shows the system 10 used for this purpose.

The system 10 includes a centrifuge assembly 12 and an associated fluid processing assembly 14. The centrifuge assembly 12 is a durable equipment item. The fluid processing assembly 14 is a single use, disposable item that the user loads on the centrifuge assembly 12 before beginning a processing procedure (as FIG. 1 generally shows) and removes from the centrifuge assembly 12 upon the completing the procedure.

The centrifuge assembly 12 comprises a centrifuge 16 mounted for rotation within a cabinet 18. The user maneuvers and transports the cabinet 18 upon the associated wheels 20. It should be appreciated that, due to its compact form, the centrifuge assembly 12 also could be made as a tabletop unit.

As FIGS. 1 and 2 show, the cabinet 18 includes a sliding drawer 36 that holds the centrifuge 16. As FIG. 1 shows, the user opens the drawer 36 to enter the centrifuge 16 for inserting and removing the processing chamber 22. As FIG. 2 shows, the user closes the drawer 36 when conducting a processing operation.

The processing assembly 14 comprises a processing chamber 22 mounted on the centrifuge 16 for rotation (as FIG. 1 shows). An associated fluid circuit 24 conveys fluids to and from the processing chamber 22. The fluid circuit 24 has several fluid containers 26. As FIG. 2 shows, in use, the containers 26 hang from a support pole outside the cabinet 18. The fluid circuit 24 transits several peristaltic pumps 28 and clamps 30 on the face of the cabinet 18. The fluid circuit 24 enters an access opening 100 leading to the processing chamber 22 mounted within the cabinet 18. In the illustrated environment, the fluid circuit 24 preconnects the processing chamber 22 with the containers 26, forming an integral, sterile unit closed to communication with the atmosphere.

Figure 10:
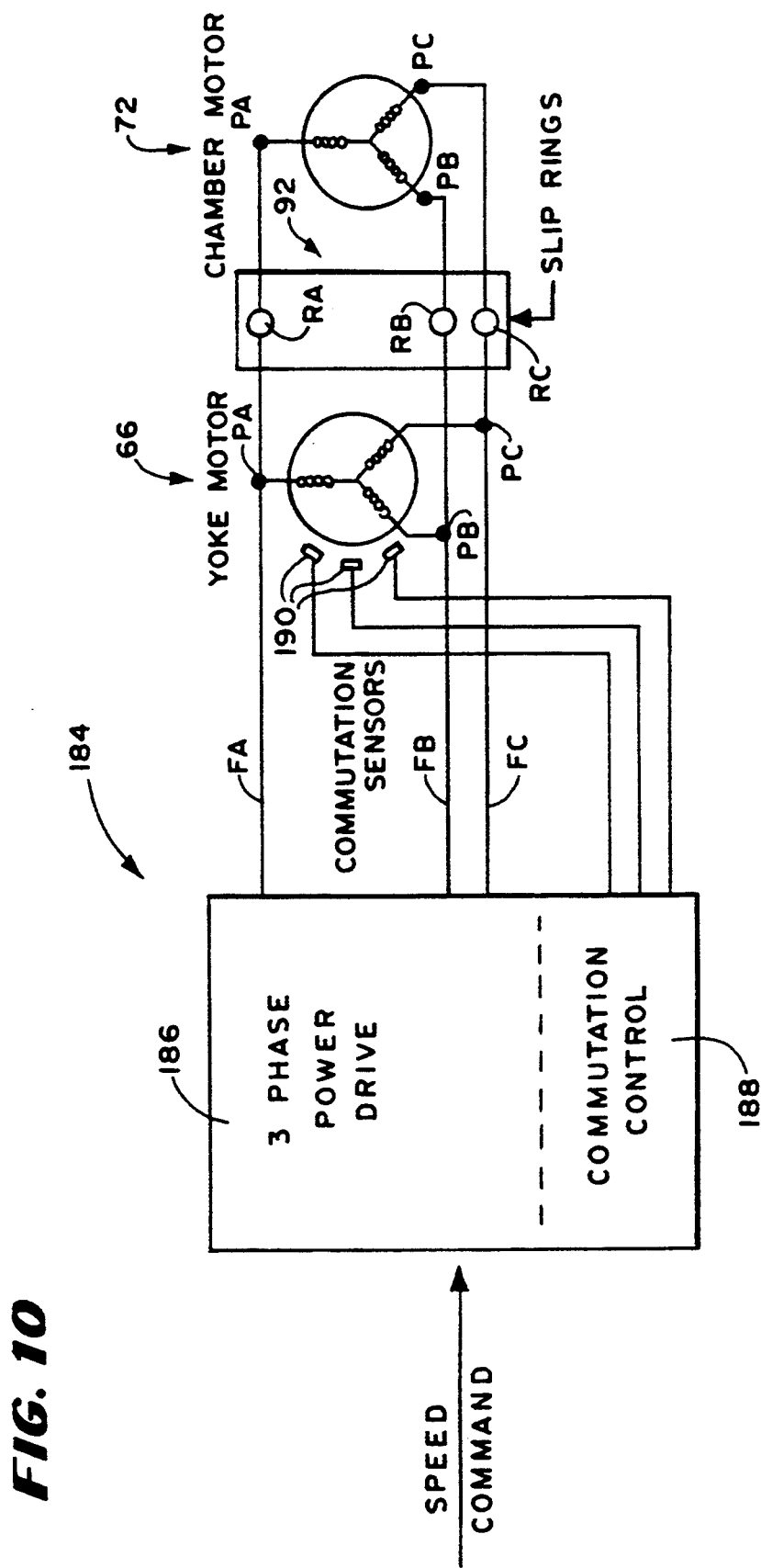
FIG. 10 is a schematic view of the drive controller for the rotating components of the centrifuge assembly.
Figure 14:
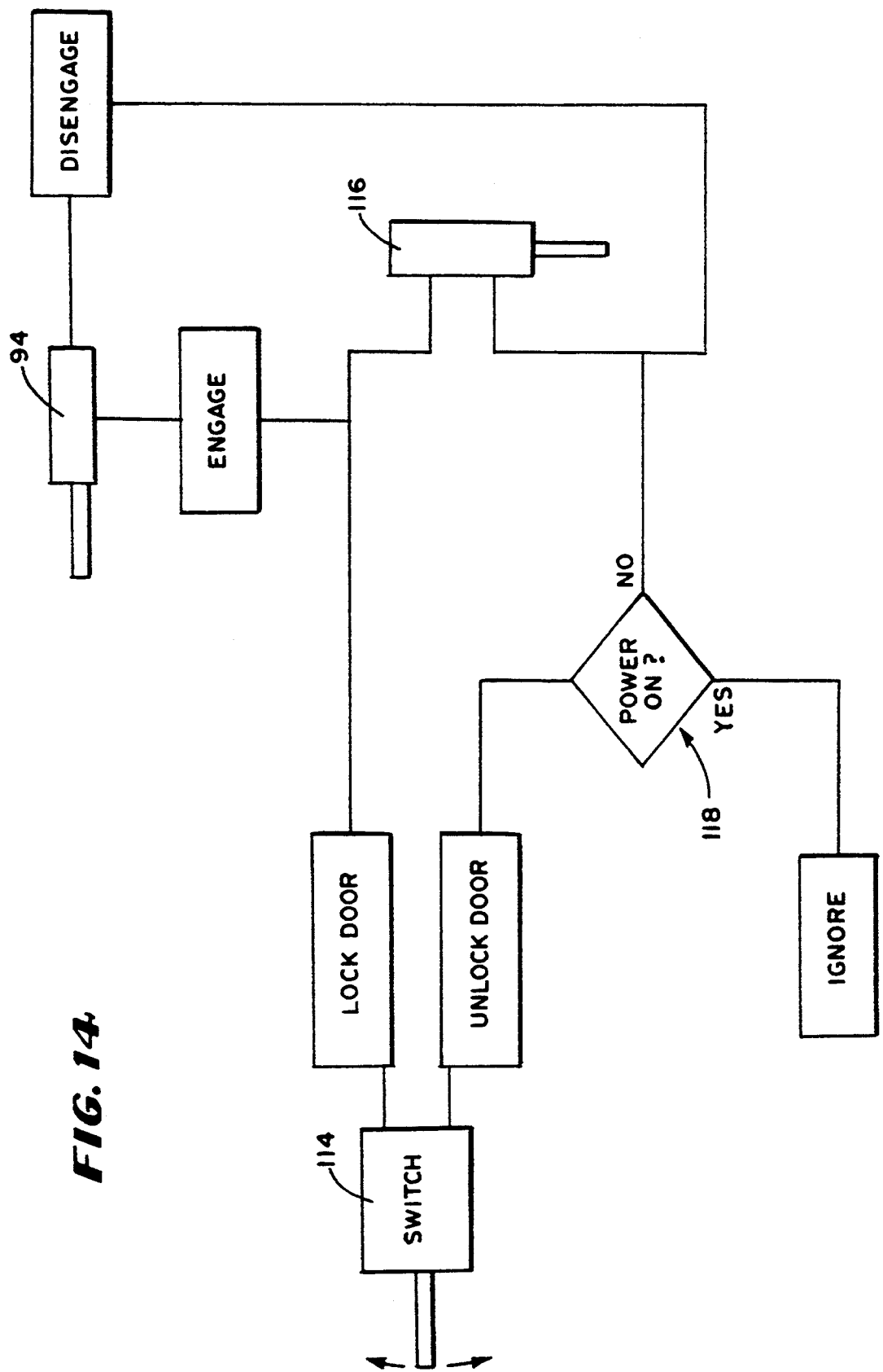
FIG. 14 is a schematic view of the drawer interlocks associated with the centrifuge assembly.

The centrifuge assembly 12 includes a processing controller 32, various details of which are shown in FIGS. 10 and 14. The processing controller 32 coordinates the operation of the centrifuge 16. The processing controller 32 preferably uses an input/output terminal 34 to receive and display information relating to the processing procedure.

The following sections disclose further details of construction of the centrifuge assembly 12, the processing assembly 14, and processing controller 32.

I. THE CENTRIFUGE ASSEMBLY

A. The One Omega Platform and Two Omega Chamber

As FIG. 3 shows, the centrifuge 16 includes a base 42 that supports a plate 45 mounted upon flexible isolation mounts 44. The flexible mounts 44 structurally isolate the components mounted on the plate 45 from the rest of the centrifuge 16, by dampening vibration and oscillation caused by these plate-mounted components. The components mounted on the plate 45 make up the isolated mass of the centrifuge 16.

A nonrotating outer housing or bucket 46 is mounted on the plate 45. The bucket 46 encloses a stationary platform 48, which in turn supports the rotating components of the centrifuge 16.

Figure 5:
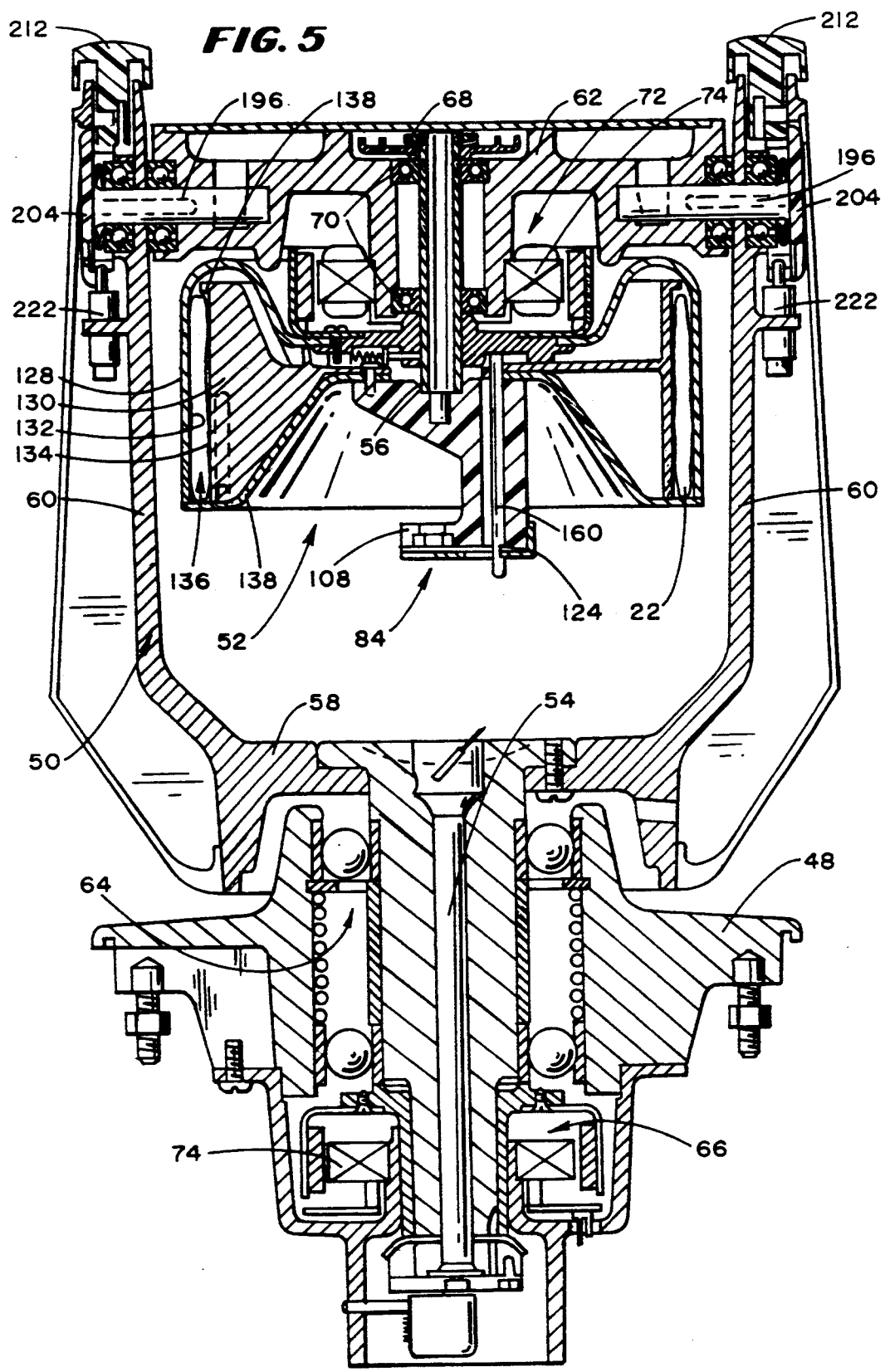
FIG. 5 is a side sectional view of the rotating components of the centrifuge assembly taken generally along line 5—5 in FIG. 4.

As FIGS. 4 and 5 show in greater detail, the rotating components include a centrifuge yoke assembly 50 and a centrifuge chamber assembly 52. The yoke assembly 50 rotates upon the platform 48 on a first drive shaft 54. The chamber assembly 52 rotates on the yoke assembly 50 on a second drive shaft 56. The rotating chamber assembly 52 carries the processing chamber 22.

The yoke assembly 50 includes a yoke base 58, a pair of upstanding yoke arms 60, and a yoke cross member 62 mounted between the arms 60. The base 58 is attached to the first drive shaft 54, which spins on a bearing element 64 about the stationary platform 48. A first electric drive 66 rotates the yoke assembly 50 on the first drive shaft 54.

The chamber assembly 52 is attached to the second drive shaft 56, which spins on a bearing element 68 in the yoke cross member 62. The second drive shaft 56 and the bearing element 68 spin as a unit on ball bearings 70. A second electric drive 72 rotates the centrifuge chamber assembly 52 on the second drive shaft.

The first electric drive 66 and the second electric drive 72 each comprises a permanent magnet, brushless DC motor. As FIG. 5 shows, the stationary platform holds the field coils 74 of the first motor 66, while the yoke base 58 comprises the armature or rotor of the first motor 66. The yoke cross member 62 holds the field coils 74 of the second motor 72, while the chamber assembly 52 comprises the associated armature or rotor.

In the illustrated and preferred embodiment, the first electric motor 66 spins the yoke assembly 50 at a predetermined speed of rotation (which will be called "one omega"). The second electric motor 72 spins the chamber assembly 52 at the same speed of rotation as the first electric motor 66 in the same direction and about the same axis as the spinning yoke assembly 50. As a result, when viewed from a stationary (i.e., non-rotating or "zero omega") position, the chamber assembly 52 spins at twice the rotational speed of the yoke assembly 50 (which will be called "two omega").

B. The Umbilicus Mounts at Zero, One, and Two Omega

As FIGS. 6 to 9 show, the fluid circuit 24 joining the processing chamber 22 and the processing containers 26 comprises separate tubes 74 joined to form an umbilicus 76. Fluids pass to and from the processing chamber 22 through these tubes 74.

Figure 6:
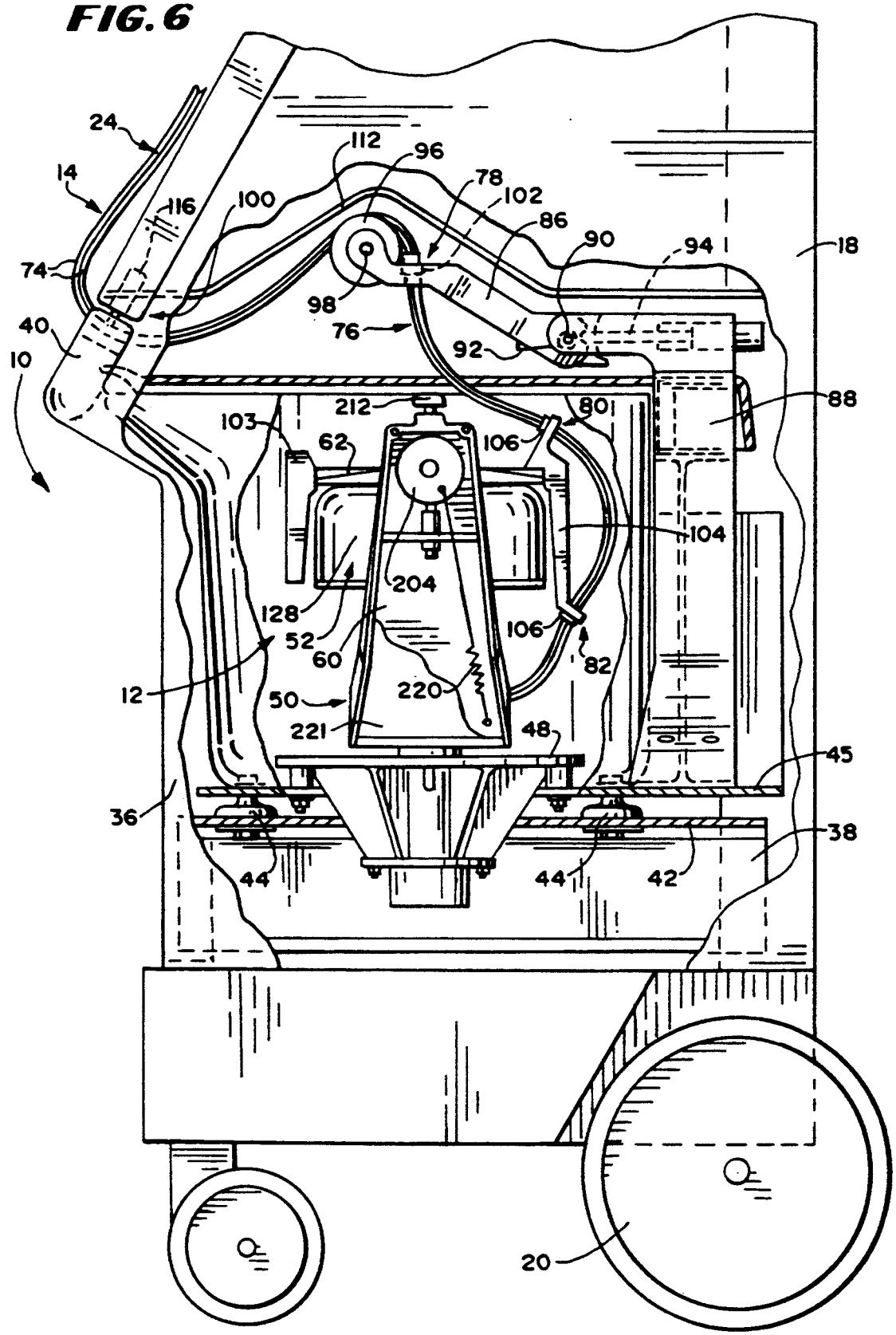
FIG. 6 is a side elevation view, with portions broken away and in section, of the rotating components of the centrifuge assembly housed within the drawer, which is shown closed.

As FIGS. 6 and 7 best show, the centrifuge 16 includes several umbilicus mounts 78, 80, 82, and 84 positioned at spaced apart zero omega, one omega, and two omega positions on the centrifuge 16. The mounts 78, 80, 82, and 84 secure the upper, middle, and lower portions of the umbilicus 76, holding it in an inverted question mark shape during processing operations.

The first umbilicus mount 78 is part of a holder 86 mounted at a zero omega position above and aligned with the rotational axis of the centrifuge 16. The mount 78 holds the upper portion of the umbilicus 76 against rotation at this position.

As FIGS. 3 and 6 best show, the zero omega holder 86 includes a support frame 88, which is itself attached to the isolation plate 45. The zero omega holder 86 therefore forms a part of the isolated mass of the centrifuge 16.

A pin 90 attaches one end of the zero omega holder 86 to the support frame 88. The holder 86 pivots on this pin 90 along the rotational axis of centrifuge 16 (as generally shown by arrows in FIG. 3). A spring 92 normally biases the holder 86 away from the rotating components 50 and 52 of the centrifuge 16. A solenoid operated latch pin 94 normally locks the holder 86 in the operating position shown in FIG. 6. It should be appreciated that, alternatively, the holder 86 can be manually locked in the operating position using a conventional over-center toggle mechanism (not shown) or the like.

The zero omega holder 86 has a roller member 96 at its opposite end. The roller member 96 rotates on a shaft 98. The roller member 96 is relieved in its mid-portion (see FIG. 8) to receive the umbilicus 76 as it enters the cabinet 18 through an access opening 100.

As FIGS. 7 and 8 best show, the first umbilicus mount 78 is located next to the roller member 96. The mount 78 comprises a channel in the holder 86 that captures an upper block 102 carried by the umbilicus 76. When locked in its operating position (shown in FIG. 6), the zero omega holder 86 applies tension on the umbilicus 76, thereby seating the upper umbilicus block 102 within the mount 78.

In the embodiment illustrated in FIGS. 7 to 9, the upper umbilicus block 102 is generally hexagonally shaped. The mount 78 is also configured as a hexagon to mate with the block 102. It should be appreciated that other mating shapes can be used to seat the umbilicus block 102 within the mount 78.

FIGS. 8A and 8B show an alternative embodiment for the zero omega holder 86. Like the holder 86 shown in FIGS. 7 and 8, the holder 86' is mounted for pivotal movement on a pin 90' to the support frame 88 (not shown in FIGS. 8A and 8B). Also like the holder 86 shown in FIGS. 7 and 8, the holder 86' has a roller member 96' and an umbilicus mount 78' located next to it. The functions of these components are as previously described.

Unlike the holder 86' shown in FIGS. 7 and 8, the holder 86' includes a mechanism for clamping the upper umbilicus block 102 within the mount 78'. While the mechanism can vary, in the illustrated embodiment, it comprises a latch member 250 mounted on pins 252 for pivotal movement on the holder 86'. FIG. 8A shows the latch member 250 in an upraised position, opening the mount 78' for receiving the upper umbilicus block 102. FIG. 8B shows the latch member 250 in a lowered position, covering the mount 78' and retaining the umbilicus block 102 therein. As FIG. 8B shows, the latch member 250 includes a relieved region that accommodates passage of the umbilicus 76 when the latch member 250 is lowered.

A pair of resilient tabs 256 on the latch member 250 mate within undercuts 258 on the holder 86' to releasably lock the latch member 250 in its lowered position. Manually squeezing in the area 260 above the resilient tabs 256 releases them from the undercuts 258.

The second and third umbilicus mounts 80 and 82 form a part of a one omega holder 104 carried on the yoke cross member 62. The mounts 80 and 82 take the form of spaced apart slotted apertures that secure the mid-portion of the umbilicus 76 to the yoke cross member 62. The mid-portion of the umbilicus 76 carries a pair of spaced apart resilient bushings 106 that snap-fit within the slotted second and third mounts 80 and 82 (see FIGS. 4 and 7). The slotted mounts 80 and 82 allow the umbilicus bushings 106 to rotate within them, but otherwise secure the umbilicus 76 as the yoke assembly 50 rotates. The yoke cross member 62 carries a counterweight 103 opposite to the one omega holder 104.

Figure 15:
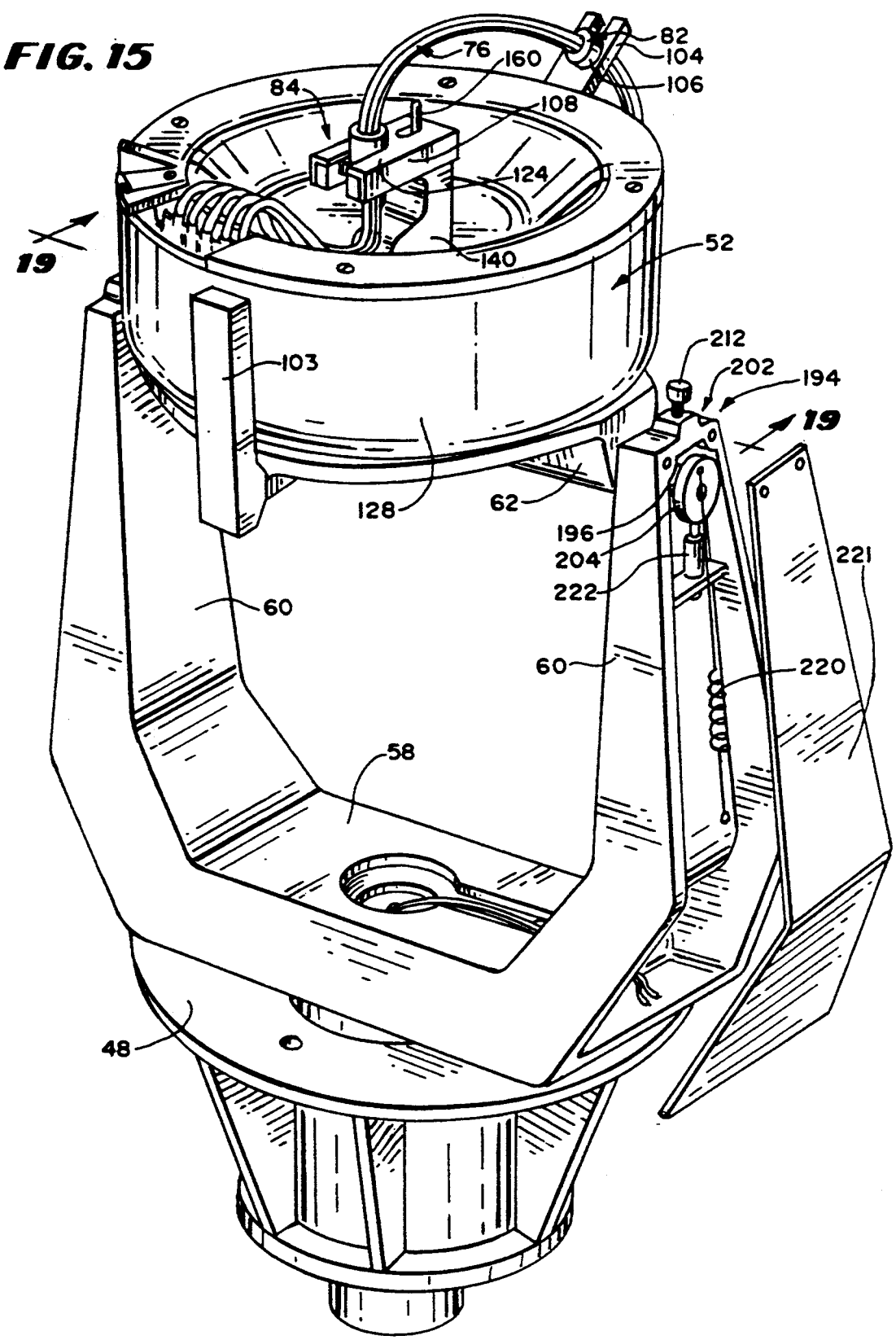
FIG. 15 is an enlarged perspective view of the rotating components of the centrifuge assembly shown in its upraised position for loading and unloading the associated processing chamber.
Figure 19:
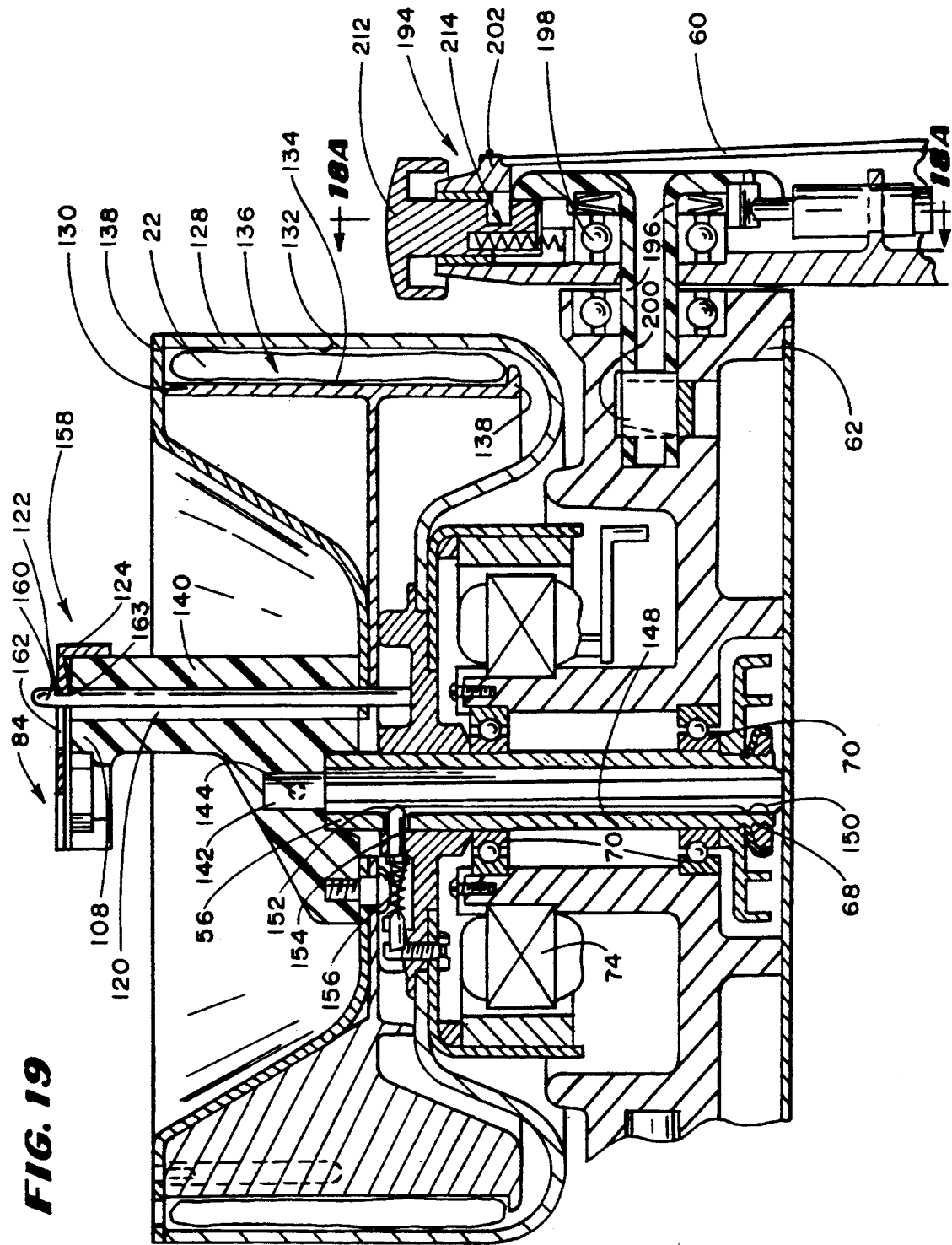
FIG. 19 is a side sectional view of the rotating components of the centrifuge assembly when in its upraised position, taken generally along line 19—19 in FIG. 15.

The fourth umbilicus mount 84 forms a part of a two omega holder 108 on the processing chamber assembly 52. As best shown in FIGS. 15 and 19, the mount 84 comprises a clamp that captures a lower block 110 carried by the umbilicus 76. The clamp mount 84 grips the lower block 110 to rotate the lower portion of the umbilicus 76 as the chamber 22 itself rotates.

In the illustrated embodiment (see FIG. 19), the lower umbilicus block 110 (like the upper umbilicus block 102) is generally hexagonally shaped. The clamp mount 84 is also configured to mate with the lower block 110 seated within it. As before pointed out, it should be appreciated that other mating shapes can be used to seat the umbilicus block 110 within the clamp mount 84.

Further details of the fourth umbilicus mount 84 will be discussed later.

The zero omega holder 86 holds the upper portion of the umbilicus in a non-rotating position above the rotating yoke and chamber assemblies 50 and 52. The holder 104 rotates the mid-portion of the umbilicus 76 at the one omega speed of the yoke assembly 50. The holder 108 rotates the lower end of the umbilicus 76 at the two omega speed of the chamber assembly 52. This relative rotation keeps the umbilicus 76 untwisted, in this way avoiding the need for rotating seals.

C. The One Omega/Two Omega Drive Control

The processing controller 32 includes an all-electrical synchronous drive controller 184 for maintaining the desired one omega/two omega relationship between the yoke assembly 50 and the chamber assembly 52. FIG. 10 shows the details of the drive controller 184.

As FIG. 10 shows, both motors 66 and 72 are three phase motors. Still, double or other multiple phase motors can be used, if desired. In the illustrated three phase arrangement, the drive controller 184 includes a three phase power driver 186. The drive controller 184 also includes a commutation controller 188 for three commutator sensors 190 associated with the first three phase electric motor 66.

The power driver 186 uses a single slip ring assembly 192 that serves the second electric motor 72. The slip ring assembly 192 includes three slip rings (designated RA, RB, and RC in FIG. 10), one associated with each pole of the second motor (designated PA, PB, and PC in FIG. 10). The slip rings RA/RB/RC serve as a conducting means for electricity. Alternative conducting means, such as a transformer coupling, could be used.

The power driver 186 includes three power feeds (designated FA, FB, and FC in FIG. 10) connected in parallel to the three poles PA/PB/PC of first electric motor 66. The power feeds FA/FB/FC operate the first motor 66 at the preselected constant one omega speed in a closed loop fashion.

The power feeds FA/FB/FC are, in turn, connected in parallel to the three poles PA/PB/PC of the second electric motor 72, each via one slip ring RA/RB/RC. The slip rings serve as a rotating electrical connector, transferring power between the first motor 66 (operating at constant speed and in a closed loop) and the second motor 72.

Since the poles PA/PB/PC of both motors 66 and 72 are connected directly together in parallel, a phase error will occur whenever the second motor 72 is not synchronous with the first motor 66. The phase error causes the two motors 66 and 72 to exchange power. Depending upon the phase angle between the counter-electromotive force (emf) voltage vector generated by the rotor and the voltage vector of the feed line, the motors 66 and 72 will either transfer power from the feed lines FA/FB/FC to the rotors (through normal motor action) or deliver power from the rotors to a feed line FA/FB/FC (through generator action).

More particularly, if the rotor of the second motor 72 (spinning the chamber assembly 52) moves ahead of the rotor of the first motor 66 (spinning the yoke assembly 50), the second motor 72 becomes a generator, delivering power to the first motor 66. Because the first motor 66 operates in a closed loop at a constant speed, this power transfer retards the rotor of the second motor 72, causing the phase error to disappear.

Similarly, if the rotor of the second motor 72 lags behind the first motor 66, the first motor 66 becomes a generator, delivering power to the second motor 72. This power transfer advances the rotor of the second motor 72, again causing the phase error to disappear.

This continuous power exchange applies a corrective torque on the rotor of the second motor 72 that either advances or retards the rotor of the second motor 72. In either case, the corrective torque eliminates any phase error between the first and second motors 66 and 72. This keeps the second motor 72 continuously in synch with and operating at the same rotational speed as the closed loop, constant speed first motor 66.

This arrangement keeps the chamber assembly 52 spinning, relative to zero omega, at exactly two omega; i.e., twice the one omega speed of the yoke assembly 50.

As the following Table illustrates, a drive controller 184 embodying the above features can be used to maintain virtual any speed ratio between two or more motors.

TABLE 1

| NUMBER OF POLES | | SPEED RATIO MAINTAINED |
|---|---|---|
| Motor 1 | Motor 2 | (Motor 2:Motor 1) |
| 2 | 2 | 2:1 |
| 4 | 4 | 2:1 |
| 6 | 6 | 2:1 |
| 8 | 8 | 2:1 |
| 2 | 4 | 3:2 |
| 2 | 6 | 4:3 |
| 4 | 8 | 3:2 |
| 4 | 6 | 5:2 |
| 6 | 2 | 4:2 |
| 6 | 4 | 5:3 |

The drive controller 184 continuously maintains the desired speed ratio without noisy and heavy geared or belted mechanical mechanisms or without complicated, sensitive electronic feedback mechanisms. The drive controller 184 allows the centrifuge 16 to be small and lightweight, yet reliable and accurate.

D. The Centrifuge Drawer

The centrifuge drawer 36 moves the entire isolated mass of the centrifuge 16 (carried on the plate 45) across the axis of rotation. The drawer 36 moves the isolated mass between an operating enclosed position (shown in FIGS. 2 and 6) and an opened position accessible to the user (shown in FIGS. 1 and 12).

When in its enclosed position, the cabinet 18 shields all sides of the isolated mass of the centrifuge 16 during operation. When in its opened position, the isolated mass of the centrifuge 18 is withdrawn from the cabinet 18. The user can access all sides of the centrifuge 16 either for maintenance or to conveniently and quickly load and unload the disposable processing assembly 14.

The centrifuge drawer 36 can be constructed in various ways. In the illustrated embodiment (as best shown in FIG. 3), the centrifuge base 42 (which supports the plate 45 upon the flexible isolation mounts 44) rides on tracks 38 within the cabinet 18. The drawer 36 includes a housing 34 attached to the isolated base 42 for movement on the tracks 38. The housing 34 has a front handle 40 that the user can grasp to move the entire isolated mass of the centrifuge 16 along the tracks 38 between the enclosed and opened positions.

The controller 32 includes a user-accessible switch 114 (see FIG. 1) that operates a latch solenoid 116 for the drawer 36. The solenoid 116 normally locks the drawer 36 to keep the centrifuge 16 in its enclosed operating position (as FIG. 6 shows). Preferable, the processing controller 32 includes an interlock 118 (see FIG. 14) that prevents operation of the solenoid 196 to unlock the drawer 36 whenever power is supplied to the centrifuge motors 66 and 72.

The interlock 118 also preferably retains the latch pin 94 in its engaged position with the zero omega holder 86 (as FIG. 6 also shows), keeping the holder 86 in its operating position during processing operations.

Figure 11:
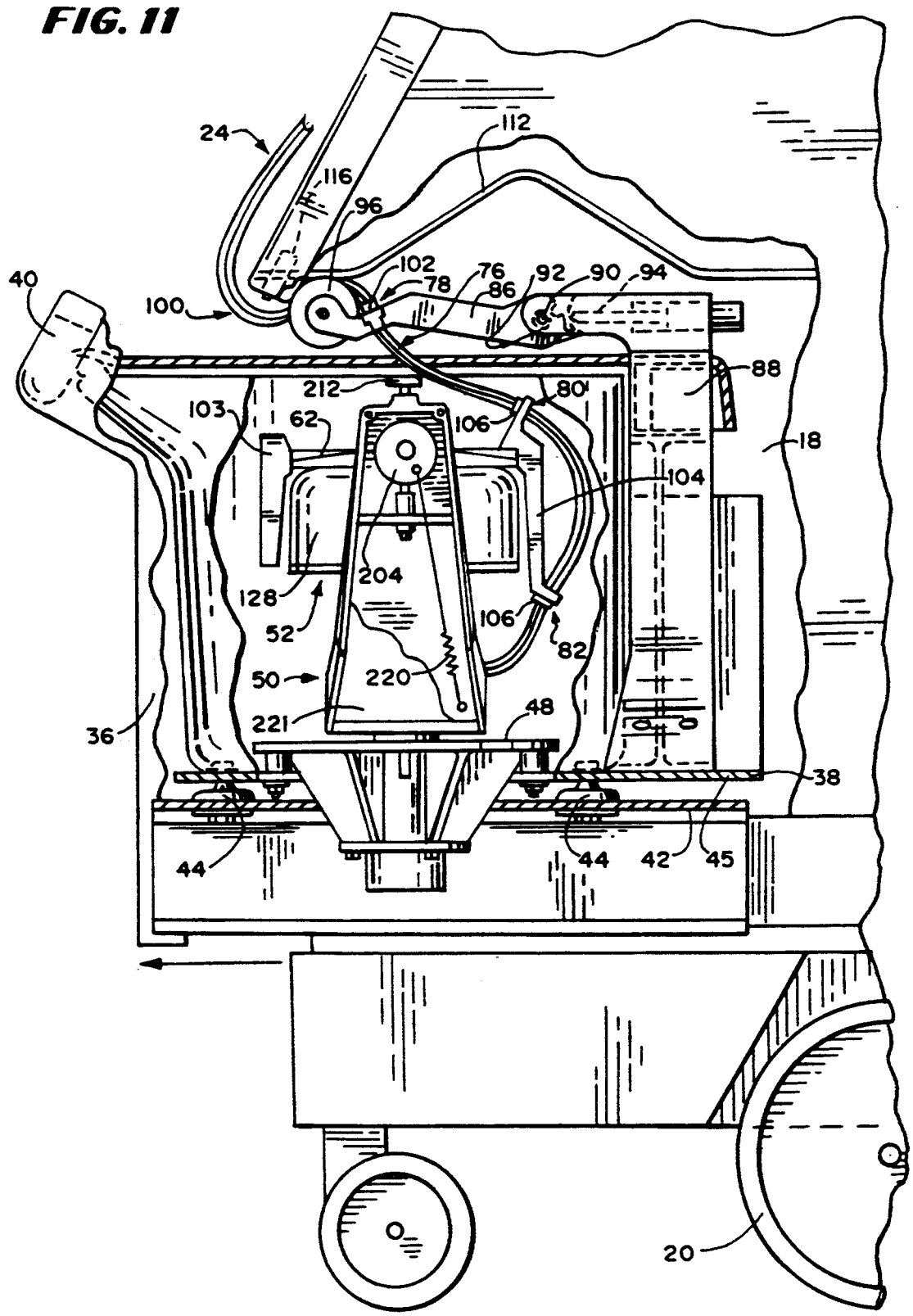
FIG. 11 is a side elevation view, with portions broken away and in section, of the rotating components of the centrifuge assembly housed within the drawer, which is shown in a partially opened condition.

When power is not being supplied to the centrifuge motors 66 and 72, operation of the switch 114 moves the solenoid 116 to its unlocked position (as FIG. 11 shows). This frees the drawer 36, allowing the user to enter the centrifuge 16. Also, the latching pin 94 withdraws, freeing the zero omega holder 86 for pivotal movement on the support frame 88.

Figure 12:
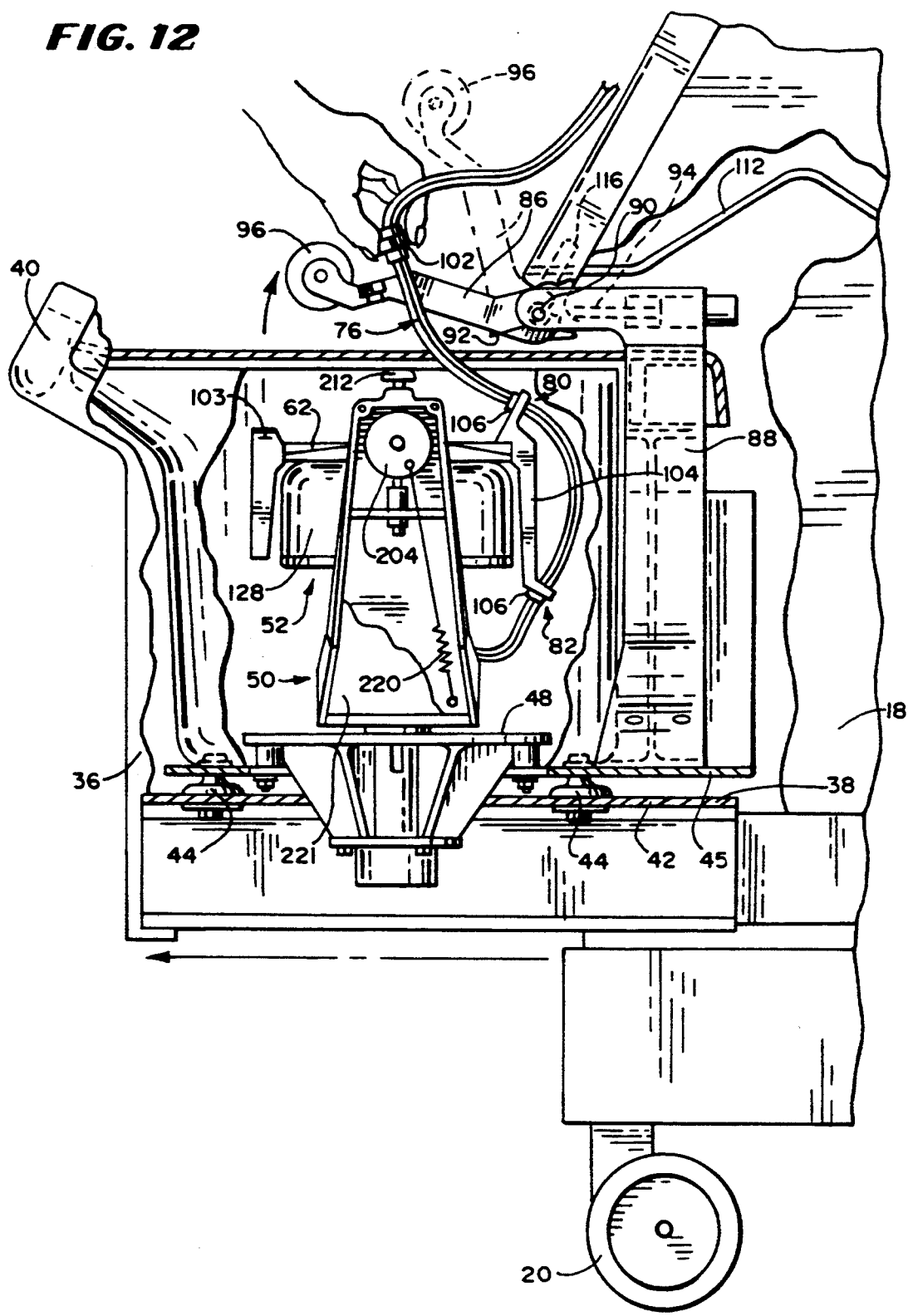
FIG. 12 is a side elevation view, with portions broken away and in section, of the rotating components of the centrifuge assembly housed within the drawer, which is shown in a fully opened condition.

As FIGS. 11 and 12 show, as the user opens the drawer 36, moving the isolated mass of the centrifuge 16 to its accessible position, the roller member 96 on the zero omega holder 86 travels along an interior ramp 112 within the cabinet 18. As the drawer 36 opens, the ramp 112 urges the zero omega holder 86 down against the biasing force of the spring 92, guiding the roller member 96 into and through the access opening 100.

Once the isolated mass of the centrifuge 16 is in its opened position (as FIG. 12 shows), the user can apply a downward force upon the spring biased zero omega holder 86 to free the upper umbilicus block 102 from the mount 78. Once freed from the block 102, the biasing spring 92 pivots the zero omega holder to a fully upraised and out-of-the-way position shown in phantom lines in FIG. 12 and in solid lines in FIG. 13.

As will be described in greater detail later, the ramp 112 also serves to guide the roller member 96 as the drawer 36 closes to return the zero omega holder 86 to its normal operating position.

E. The Two Omega Chamber Assembly

Figure 13:
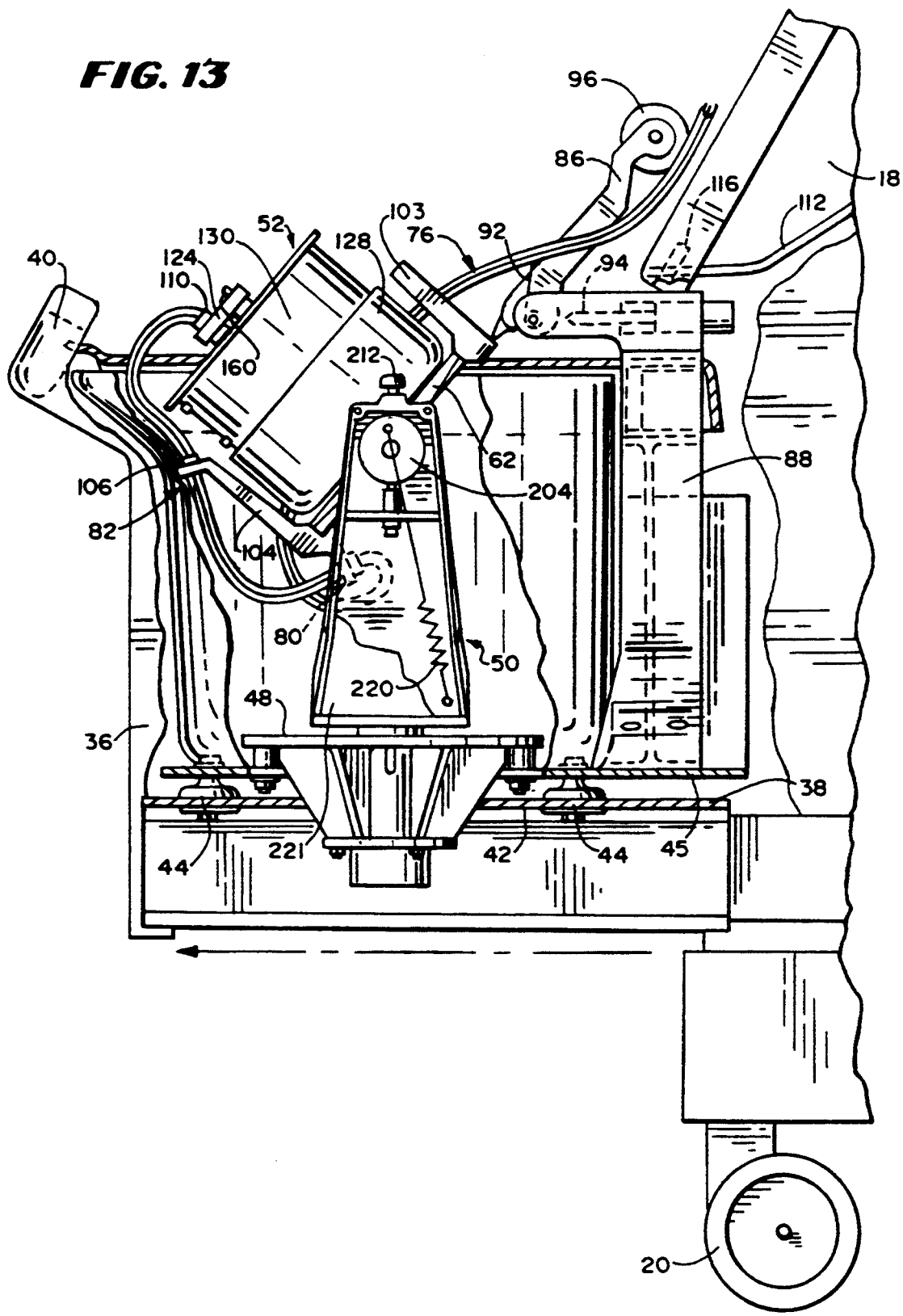
FIG. 13 is a side elevation view, with portions broken away and in section, of the rotating components of the centrifuge assembly housed within the drawer, which is shown in a fully opened condition, with the centrifuge assembly upright and opened for loading and unloading the associated processing chamber.

As FIG. 13 shows, once the centrifuge 16 occupies its accessible position outside the cabinet 18, the user can pivot the entire processing chamber assembly 52 about the yoke cross member 62 to an upright position convenient for loading and unloading the processing chamber 22 (FIG. 1 shows this, too). As FIG. 13 also shows, once in its upright position, the user can further open the entire processing chamber assembly 52 to further simplify loading and unloading operations.

1. Pivoting the Chamber Assembly for Loading

FIGS. 15 to 18A/B/C show the details of the pivot assembly 194 for moving the processing chamber 52 into its upright position.

The pivot assembly 194 suspends the yoke cross member 62 between the yoke arms 60. The two omega chamber assembly 52 carried on the cross member 62 thereby rotates between a downward suspended position (shown in FIG. 4) and an upright position (shown in FIG. 15).

When operating, the chamber assembly 52 occupies the suspended position. The user places the chamber assembly 52 in the upright position for loading and unloading the processing chamber 22 after having placed the isolated mass of the centrifuge 16 is in its accessible opened position outside the cabinet.

The pivot assembly 194 for the chamber assembly 52 may be constructed in various alternative ways. FIGS. 15 to 18A/B/C to 18 show the details of one preferred embodiment. The Figures show only one side of the pivot assembly 194 in detail, because the other side is constructed in the same manner.

The pivot assembly 194 includes a pair of left and right pivot pins 196. Bearings 198 carry the pivot pins 196 on the yoke arms 60. A retainer bracket 200 secures each pivot pin 196 to the yoke cross member 62.

The pivot assembly 194 employs a swinging lock assembly 202 to control the extent and speed of rotation of the chamber assembly 52 on the pivot pins 96. The swinging lock assembly 202 includes a rotating cam 204 secured to the end of each pivot pin 196. Each cam 204 includes a cut out arcuate groove 206 (see FIG. 16) that ends at opposite first and second detents, respectively 208 and 210. The groove 206 defines the range of rotation of the chamber assembly 52 on the pivot assembly 194.

The swinging lock assembly 202 also includes left and right locking pins 212 carried in the top of each yoke arm 60. Each locking pin 212 has an end key 214 that rides within the interior groove 206 of the associated cam 204. The opposite end of each locking pin 212 forms a control button for manipulation by the user at the top of the upright yoke arms 60.

Figure 18A:
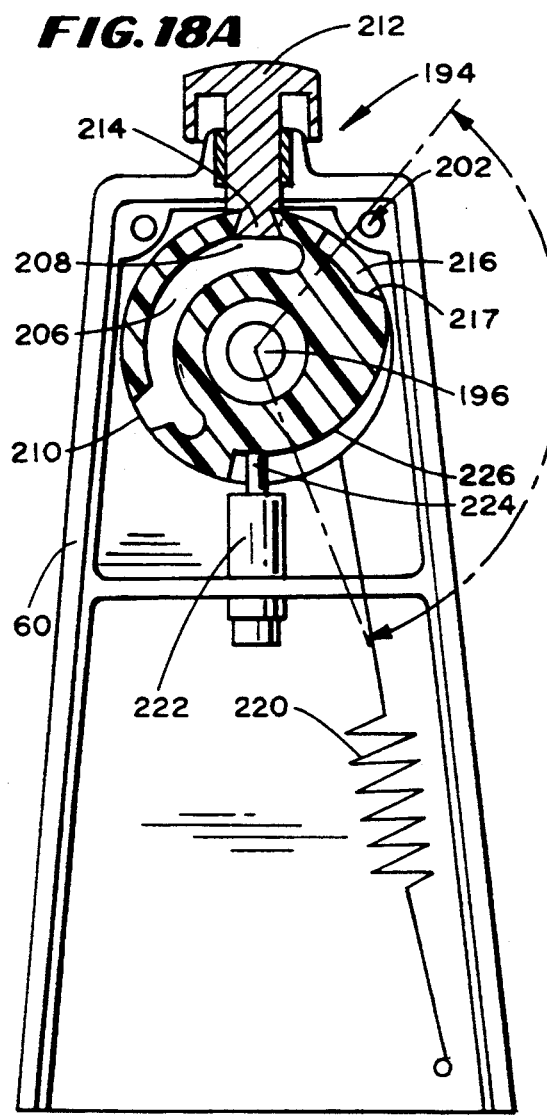
FIGS. 18A; 18B; and 18C are a series of side section views showing the operation of the swinging lock assembly.
Figure 18B:
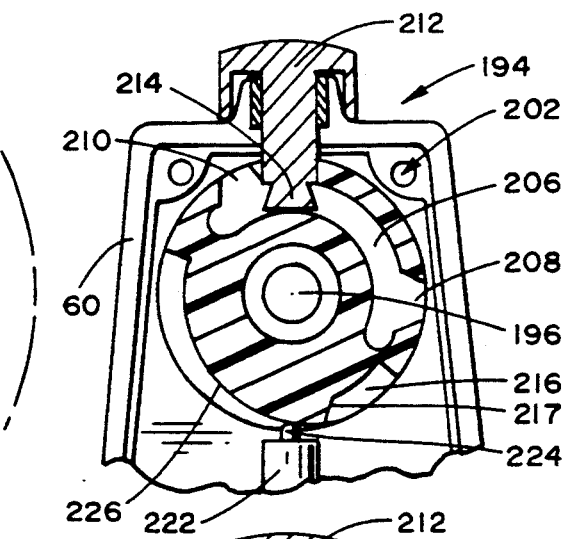

The user can independently move each locking pin 212 between an upraised position (shown in FIGS. 18A and 18C) and a depressed position (shown in FIG. 18B). The swinging lock assembly 202 uses a spring 218 to normally bias each locking pin 212 toward its upraised position.

When in its upraised position, the end key 214 of each locking pin 212 is captured within either the first detent 208 or the second detent 210 of the associated cam 204, depending upon the rotational position of the cam 204. When captured by either detent 208/210, the end key 214 prevents further rotation of the associated cam 204. When in its upraised position, the end key 214 locks the chamber assembly 52 into either its upright load position or its suspended operating position.

More particularly, when the first detent 208 captures the end key 214 of at least one locking pin 212 (as FIG. 18A shows), the locked cam 204 holds the chamber assembly 52 in its suspended operating position (shown in FIG. 4). When the second detent 210 captures the end key 214 of at least one locking pin 212 (as FIG. 18C shows), the locked cam 204 holds the chamber assembly 52 in its upraised load position (shown in FIG. 15).

When the user depresses the locking pin 212 (as FIG. 18B shows), the end key 214 moves out of the detent 208/210 and into the groove 206, freeing the associated cam 204 for rotation within the limits of groove 206. By freeing the end keys 214 of both locking pins 212 from their associated detents 208/210, the user pivots the chamber assembly 52 between its operating and load positions. Upon rotation from one detent position to the other, the biasing springs 218 automatically snap the end key 214 of each the locking pin 212 into the other detent as it reaches alignment with the end key 214, thereby automatically locking the chamber assembly 52 in the other detent position.

In the illustrated and preferred embodiment, the swinging lock assembly 202 also includes a biasing spring 220 associated with each cam 204. The springs 220 rotationally bias the cams 204 toward the position shown in FIG. 18C, where the second detent 210 captures the end keys 214 of the locking pins 212. Together, the springs 220 bias the chamber assembly 52 toward its upraised load position.

Figure 18C:
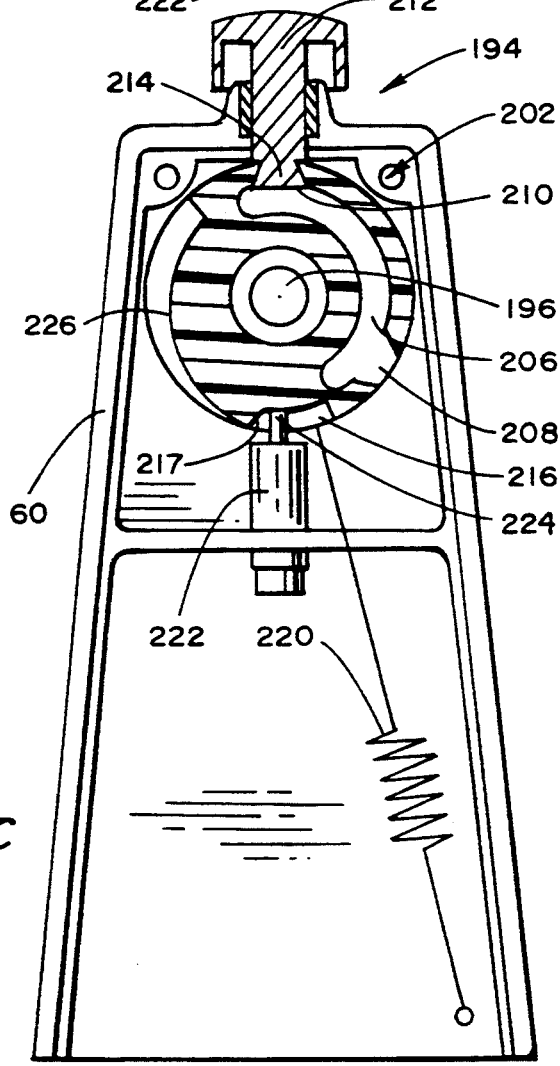

In this arrangement, by depressing both locking pins 212 with the chamber assembly 52 located in its downward operating position (FIG. 18A), the freed cams 204 automatically swing the chamber assembly 52 in response to the springs 220 into its upraised load position (FIG. 18C).

The swinging lock assembly 202 also preferably includes a damping cylinder 222 associated with each spring assisted cam 204. The damping cylinder 222 has a spring or pressure operated pin 224 that continuously presses against an outwardly radially tapered damping surface 226 on each cam 204. As it rides upon the tapered damping surface 226, the pin 224 progressively resists the spring-assisted rotation of each cam 204, moving from the first detent 208 (the downward operating position) toward the second detent 210 (the upraised load position). The progressive resistance of the pin 224 slows the pivotal movement of the assembly 52, as the pin 224 comes to rest at the outermost radius of the ramp 226 (as FIG. 18B shows), which amounts to about 100 degrees of rotation from the suspended operating position. The user then pulls on the processing chamber 52 to rotate it about an additional 30 degrees to slip the pin 224 into a retaining notch 216 (as FIG. 18C shows). There, the biasing springs 218 of each locking pin 212 snap the end keys 214 into the second detents 210, locking the chamber assembly 52 in its upraised load position.

With the chamber assembly 52 located in its upraised position, the user can simultaneously depress both locking pins 212. The chamber assembly 52 will rotate about 30 degrees, until the pin 224 abuts against the ramped portion 217 of the notch 216. The user is then free to release the locking pins 212 without engaging the second detents 210 and manually pivot the chamber assembly 52 to free the pin 224 from the retaining notch 216. Further rotation against the action of the biasing springs 220 brings the chamber assembly 52 back to its operating position. There, the biasing springs 218 of each locking pin 212 snap the end keys 214 into the first detents 208 of the cams 204, preventing further rotation out of this position during processing.

As FIG. 15 shows, a protective cover 221 is preferably mounted on each side of the yoke arms 60 to enclose the pivot assembly 194 and associated components. This protective cover 221 has been removed or cut away in some of the drawings to simplify the discussion.

2. Opening the Chamber Assembly for Loading

Figure 20:
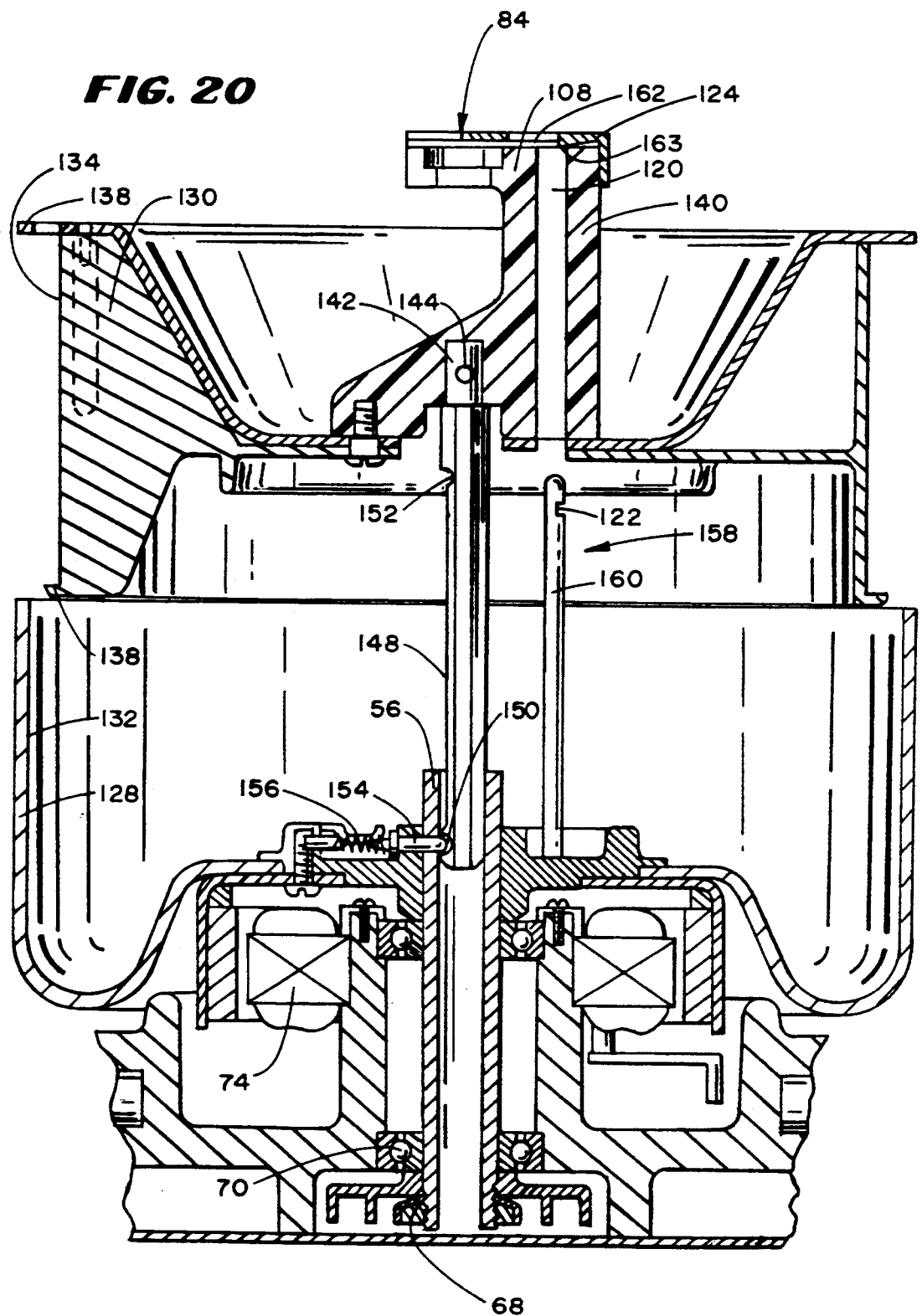
FIG. 20 is a side sectional view of the rotating components of the centrifuge assembly when in its upraised and open position.

As FIGS. 13, 19 and 20 show, when locked in its upraised position, the user also can open the chamber assembly 52 for loading and unloading the replaceable processing chamber 22 in the manner shown in FIG. 1.

For this purpose, the chamber assembly 52 includes a rotating outer bowl 128 that carries within it an inner spool 130. In use, the inner spool 130 holds the processing chamber 22. The inner spool 130 telescopically moves into and out of the outer bowl 128 to allow the mounting and removal of the chamber 22 upon the spool 130.

The outer bowl 128 has a generally cylindrical interior surface 132. The inner spool 130 has an exterior peripheral surface 134 that fits telescopically within the outer bowl surface 132 (see FIG. 9). An arcuate channel 136 extends between the two surfaces 132 and 134. When mounted on the spool 130, the processing chamber 22 occupies this channel 136. The spool 130 preferably includes top and bottom flanges 138 to orient the processing chamber 22 within the channel 136.

The centrifuge assembly 12 includes a mechanism for moving the inner spool 130 into and out of the bowl 128. The mechanism can be variously constructed, and FIGS. 19 to 24 show one preferred arrangement.

As FIGS. 19 and 20 show, the outer bowl 128 is coupled to the second drive shaft 56. The inner spool 130 includes a center hub 140. A spool shaft 142 is secured to the hub 140 by a pin 144. The spool shaft 142 fits telescopically within the open bore of the second drive shaft 56.

The exterior surface of the spool shaft 142 has a hexagonal shape (as FIG. 21 best shows). The interior bore at the base 146 of the second drive shaft 56 has a mating hexagonal shape. The mating hexagonal surfaces couple the spool 130 to the bowl 128 for common rotation with the second drive shaft 56.

In the arrangement, the inner spool 130 is movable along the second drive shaft 56 between a lowered operating position within the outer bowl 128 (as FIG. 19 shows) and an unlifted loading position out of the outer bowl 128 (as FIG. 20 shows). As FIG. 21 best shows, the hub 140 preferably takes the shape of a handle that the user can easily grasp to raise and lower the spool 130.

As FIGS. 19 and 20 show, the spool shaft includes an axial keyway 148 having a lower detent 150 and an upper detent 152. The keyway 148 defines the range of up and down movement of the spool 130 within the bowl 128.

The bowl 128 includes a detent pin 154 that extends into the open bore of the second drive shaft 56. A spring 156 biases the detent pin 154 into the keyway 148, where it rides into and out of releasable engagement with the lower and upper detents 150 and 152 as the user raises and lowers the spool 130.

In this arrangement, when the upper detent 152 engages the spring biased pin 154 (as FIG. 19 shows), the spool 130 is releasably retained in its lowered operating position. When the lower detent 150 engages the spring biased pin 154 (as FIG. 20 shows), the spool 130 is releasably retained in its uplifted loading position. Normal external lifting and lowering force exerted by the user overcomes the biasing force of the spring 156 to easily move the spool 130 up and down between these two limit positions.

With the spool 130 locked in its uplifted position, the user can wrap the processing chamber 22 upon the peripheral spool surface 134 (as FIG. 1 shows). With the spool 130 locked in its lowered position (see FIG. 19), the wrapped processing chamber 22 is sandwiched within the channel 136 between the spool 130 and the bowl 128. Rotation of the chamber assembly 52 subjects the processing chamber 22 to centrifugal forces within the channel 136.

A locking mechanism 158 prevents the spool 130 from dropping out of the bowl 128 while the chamber assembly 52 rotates in its downward suspended operating position.

The mechanism 158 includes locking pin 160 fastened to the bowl 128. The distal end of the locking pin 160 extends out through a passage 120 in the hub 140. The distal end includes a notch 122.

As FIGS. 21 and 22 show, a latch member 124 slides on tracks 126 upon the handle end of the hub 140. The notched distal end of the locking pin 160 passes through an elongated slot 162 in the latch member 124. Springs 164 normally bias the latch member 124 toward a forward position on the handle end of the hub 140. In this position (shown in FIG. 24), the notch 122 engages the rear edge 163 of the slot 162. This engagement secures the spool 130 to the bowl 128. The latch member 124 is mass balanced so that centrifugal force will not open it during use.

As FIG. 23 shows, sliding the latch member 124 rearward frees the notch 122 from the rear slot edge 163. This releases the spool 130 from the bowl 128, allowing the user to lift the spool 130 from the bowl 120 in the manner previously described.

In the embodiment shown in FIGS. 19 to 24, the sliding latch member 124 also forms a part of the two omega umbilicus clamp mount 84. As FIGS. 21 and 23 show, sliding the latch member 124 rearward opens the mount 84 to receive the lower umbilicus block 110. The spring assisted return of the latch member 124 to its forward position (shown in FIG. 24) captures the lower umbilicus block 110 within the mount 84. The biasing springs 164 also hold the latch member 124 closed to clamp the block 110 within the mount during processing operations.

In this arrangement, the locking pin 160 is preferably flexible enough to be resiliently displaced by the user (as the phantom lines in FIG. 24 show) to free the notch 122 from the rear slot edge 163 without operating the latch member 124. This allows the user to lift the spool 130 into its upraised position without freeing the lower umbilicus block (as FIG. 13 shows).

As FIGS. 22 and 23 also show, the latch member 124 is preferably vertically moveable within the tracks to drop the rear slot edge 163 into engagement against the rear edge 166 of the hub handle. This allows the user to temporarily secure the latch member 124 in its rearward position against the action of the biasing springs 164, freeing both of the user's hands to load the umbilicus 76. Lifting upward frees the rear slot edge 163, allowing the springs 164 to return the latch member 164 to its forward clamping position.

Figure 26:
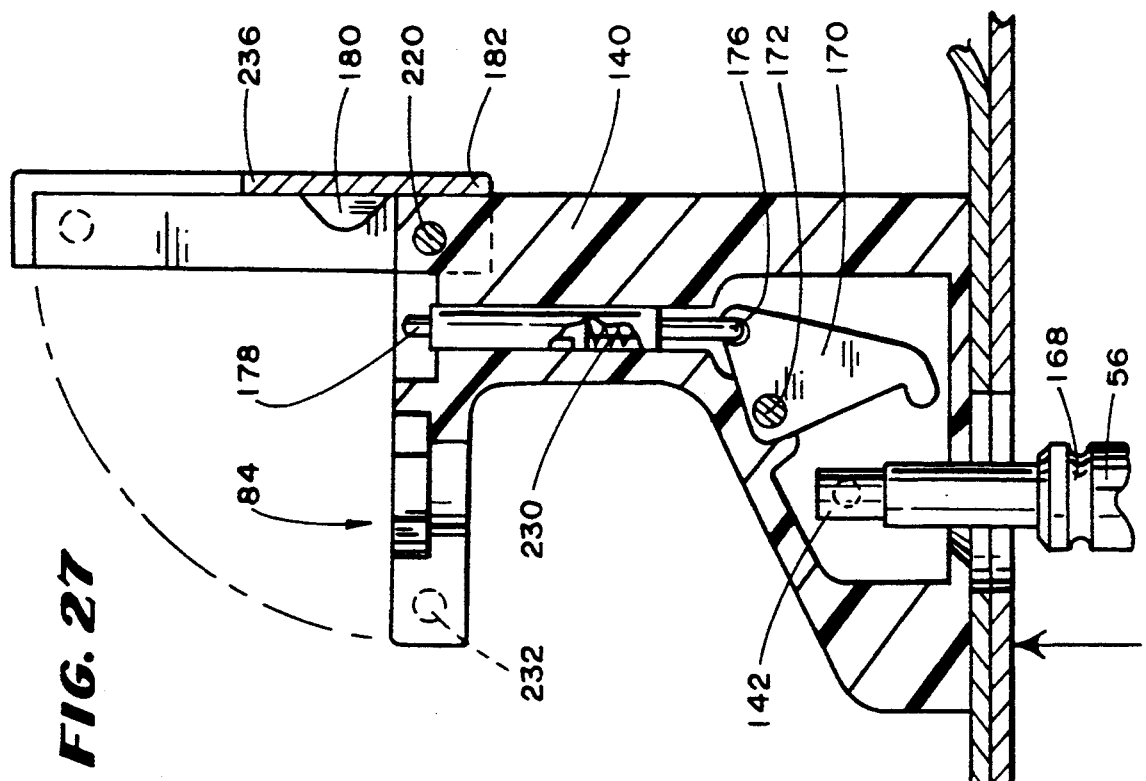
FIGS. 26 and 27 are side sectional views showing the operation of the mechanism shown in FIG. 25.
Figure 27:
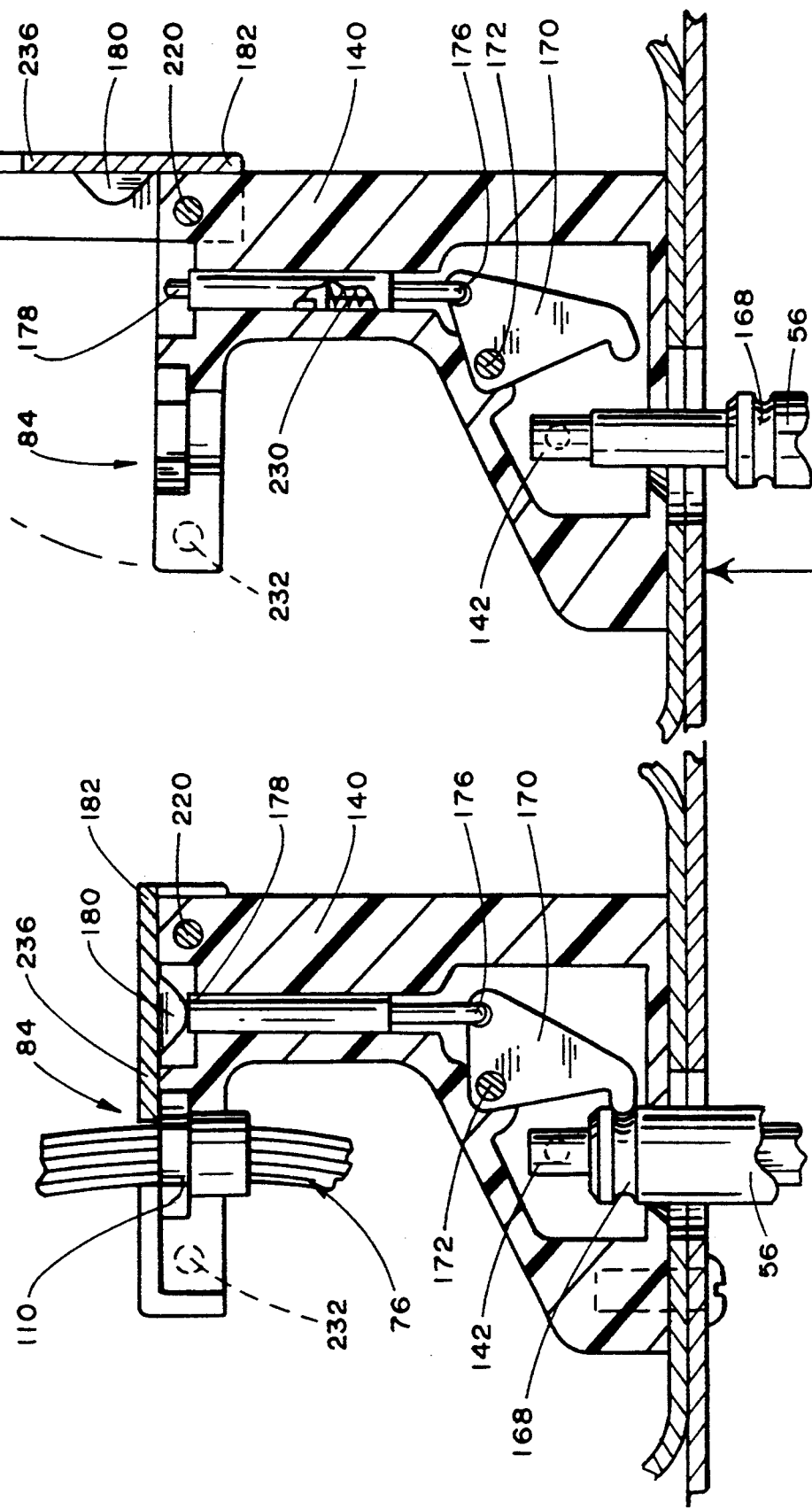

FIGS. 25 to 27 show an alternative locking mechanism 158 for the spool 130. In this arrangement, the second drive shaft 56 includes an undercut latchway 168. The hub 140 houses a latch pawl 170 carried by a pin 172 for pivotal movement between an engaged position with the latchway 168 (as FIG. 26 shows) and a disengaged position from the latchway 168 (as FIGS. 25 and 27 show).

The hub 140 carries linkage 174 that operates the latch pawl 170. The linkage 174 has a hooked end 176 coupled to the latch pawl 170 and a pin end 178 positioned in the path of a cam 180 carried by a latch lever 182. A pin 228 attaches the latch lever 182 to the hub 140 for pivotal movement between an unlatched position (shown in FIGS. 25 and 27) and a latching position (shown in FIG. 26).

A spring 230 normally biases the linkage 190 to maintain the latch pawl 170 in its disengaged position when the latch lever 182 is in its unlatched position. In this orientation, the user is free to raise the spool 130 in the manner just described.

With the spool 130 in its lowered position, movement of the latch lever 182 to the latching position brings the cam 180 into contact with the pin end 178. Depressing the pin end 178 in turn moves the linkage 174 against the biasing force of the spring 230 to pivot the latch pawl 170 into its engaged position with the latchway 168. In this orientation, the interference between the latch pawl 170 and the latchway 168 prevents axial movement of the spool 130 along the second drive shaft.

When the latch lever 182 is in its latching position, spring biased pins 232 releasably engage detents 234 on the latch lever 182. The pins 232 releasably resist movement of the latch lever 182 out of its latching position. By applying deliberate lifting force to the latch lever 182, the user can overcome the spring biased pins 232 to move the latching lever 182 into its unlatched position.

In this arrangement, a holding bracket 236 associated with the latch lever 182 locks the lower umbilicus block 110 within the mount 84 while the spool 130 is locked into its lowered position. In this embodiment, the holding bracket 236 opens the mount 84 when the latch lever 182 is in its unlatched position (shown in FIG. 25) and closes the mount 84 when the latch lever 182 is in its latching position (shown in FIG. 26).

F. Loading the Fluid Processing Assembly

FIGS. 28 to 31 show the details of loading a representative processing assembly 14 on the centrifuge 16, as is generally depicted in FIG. 1. The representative processing assembly 14 includes a processing chamber 22 formed as an elongated flexible tube or belt made of a flexible, biocompatible plastic material such as plasticized medical grade polyvinyl chloride. The umbilicus tubes 74 communicate with ports 248 to conduct fluids into and out of the processing chamber 22.

The user begins the loading process by wrapping the flexible processing chamber 22 about the upraised and open spool 130.

Figure 28:
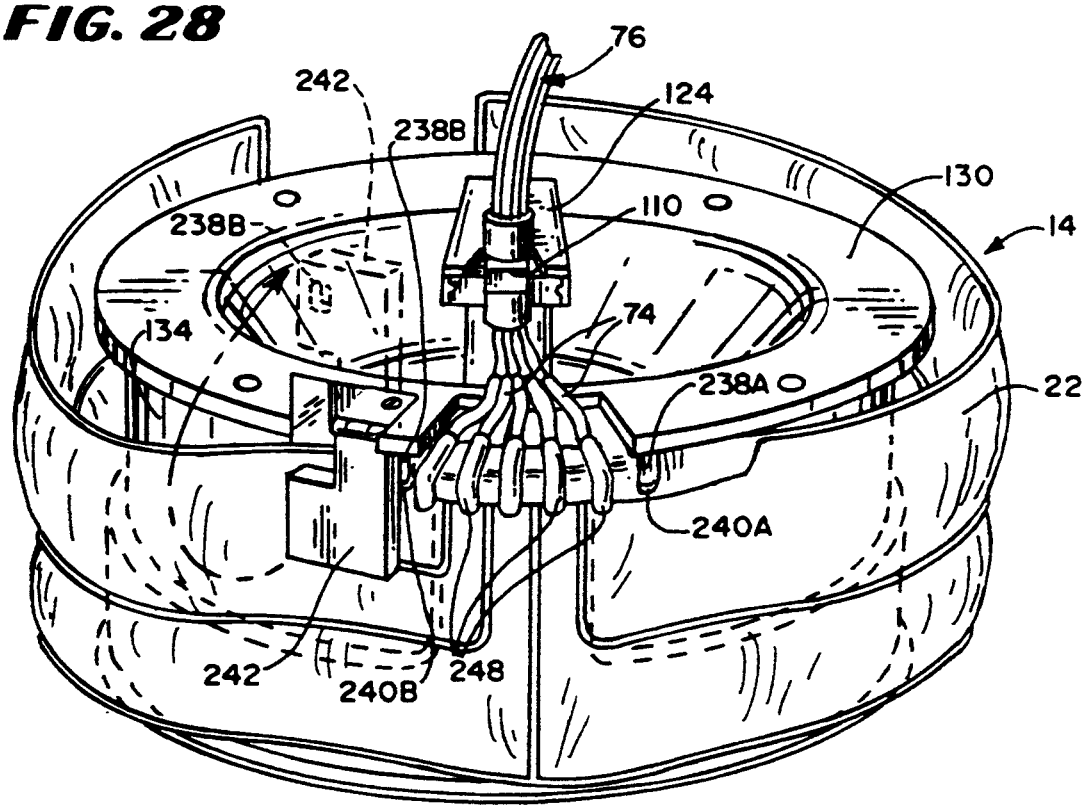
FIG. 28 is a perspective view of the processing chamber as it is being wrapped onto the centrifuge spool prior to use.

As FIG. 28 best shows, the spool 130 includes one or more alignment tabs 238 on the spool 130. The spool alignment tabs 238 register with alignment notches 240 on the processing chamber 22 to assure the desired orientation of the processing chamber 22 on the spool 130.

Of course, the ways of aligning the chamber 22 on the spool 130 can vary. In the illustrated embodiment, the spool 130 has two alignment tabs 238A and 238B, and the processing chamber 22 has two mating alignment notches 240A and 240B. Alternatively, pins or other alignment mechanisms can be used.

As FIG. 28 shows, one spool alignment tab 238A protrudes from the spool surface 134 and mates with the notch 240A on the processing chamber 22. The other spool alignment tab 238B protrudes from a flap 242 that extends from and overhangs a portion of the spool surface 134.

In the illustrated embodiment, the flap 242 is hinged. It is movable between a raised position (shown in phantom lines in FIG. 28), away from the spool surface 134, and a lowered position (shown in solid lines in FIG. 28), facing toward the spool surface 134. By placing the flap 242 into its lowered position, the alignment tab 238B on the flap 242 fits within a retainer 244 in the spool surface 134.

In this arrangement, with the flap 242 upraised, the user aligns the notch 240A with the tab 238A and aligns the notch 240B over the retainer 244. Lowering the flap 242 places the tab 238B into the retainer 244, capturing the notch 240B between the flap 242 and the spool surface 134 (as FIG. 28 shows) to hold the processing chamber 22 in place.

Instead of a hinged flap 242, a flap fixed in the lowered position can be used. In this arrangement, the user tucks the processing chamber 22 beneath the flap.

Figure 29:
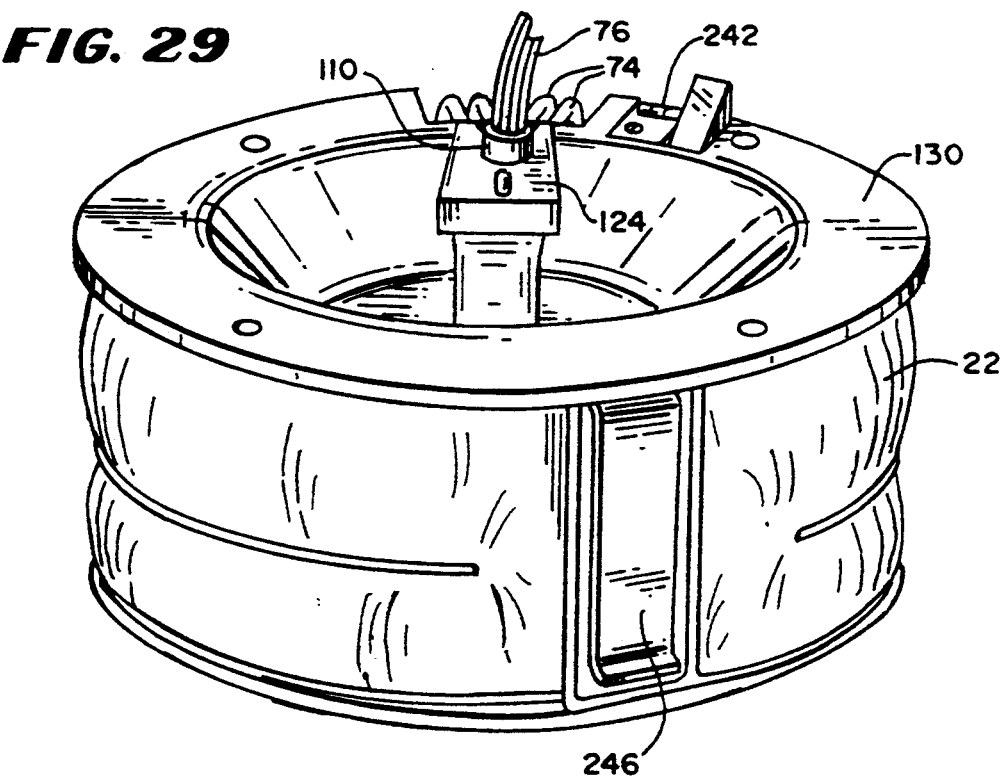
FIG. 29 is a perspective view of the processing chamber wrapped on the centrifuge spool for use.

As FIG. 29 shows, the user completes the loading process by overlapping the free ends of the processing chamber 22 on the opposite side of the spool 130. A clip 246 captures the overlapping ends, holding them close against the spool surface 134. Alternatively, an adhesive tab (not shown) can be used to hold the overlapping ends of the processing chamber 22 together, as could pins mating with associated holes in the processing chamber 22.

Figure 30:
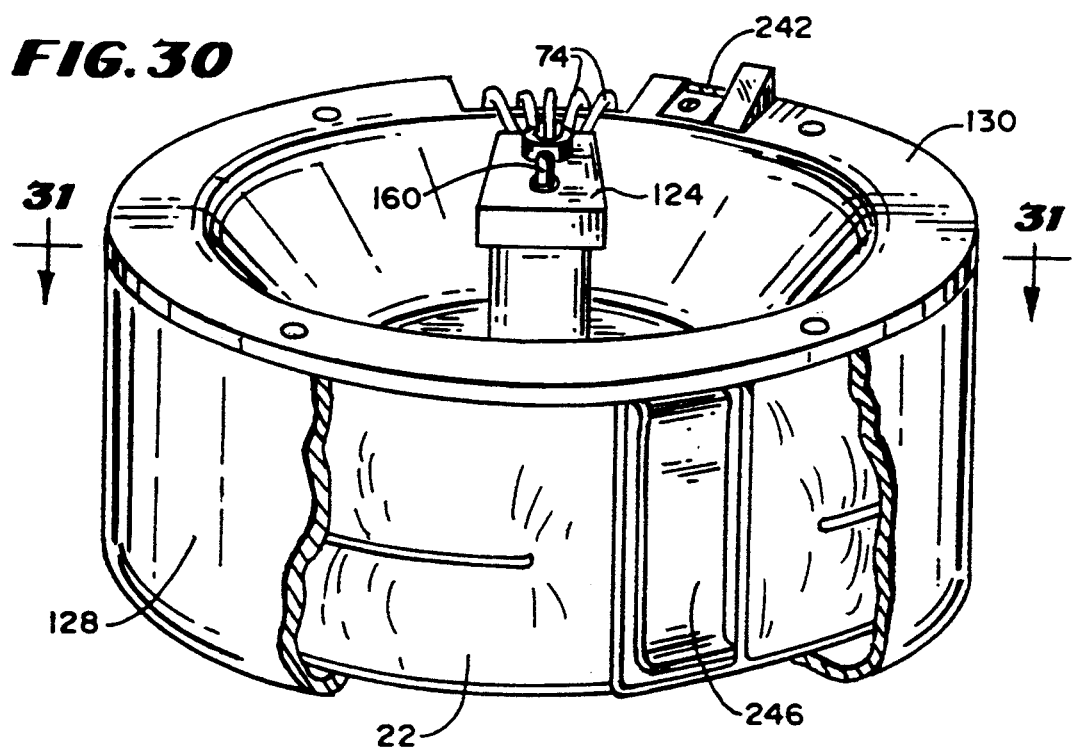
FIG. 30 is a perspective view, with portions broken away, of the centrifuge spool holding the processing chamber and in position within the centrifuge bowl for use.

The user then lowers and locks the spool 130 within the bowl 128 in the manner previously described to complete the loading process (as FIG. 30 shows). The user clamps the lower umbilicus block 110 into the mount 84 in the manner previously described and pivots the chamber assembly 52 into its downward suspended position shown in FIG. 4.

The user then snaps the umbilicus bushings 106 into position in the slotted second and third mounts 80 and 82 on the one omega holder 104, as FIG. 4 shows. The user lowers the zero omega holder 86 toward the rotating components 50 and 52 of the centrifuge 16 to seat the upper block 102 into the mount 78.

The user closes the drawer 36 and completes the loading process by placing the tubes 74 into operative alignment with the pumps 28 and clamps 30 on the front panel of the cabinet 18.

The user generally follows a reverse sequence of steps to unload the fluid processing assembly 14.

G. Shaping the Processing Chamber

The interior bowl surface 132 and the exterior spool surface 134 are preformed to create within the high-G and low-G regions of the processing chamber 22 the specific contours required either to get the desired separation effects or to achieve optimal priming and air purging, or both.

Figure 32:
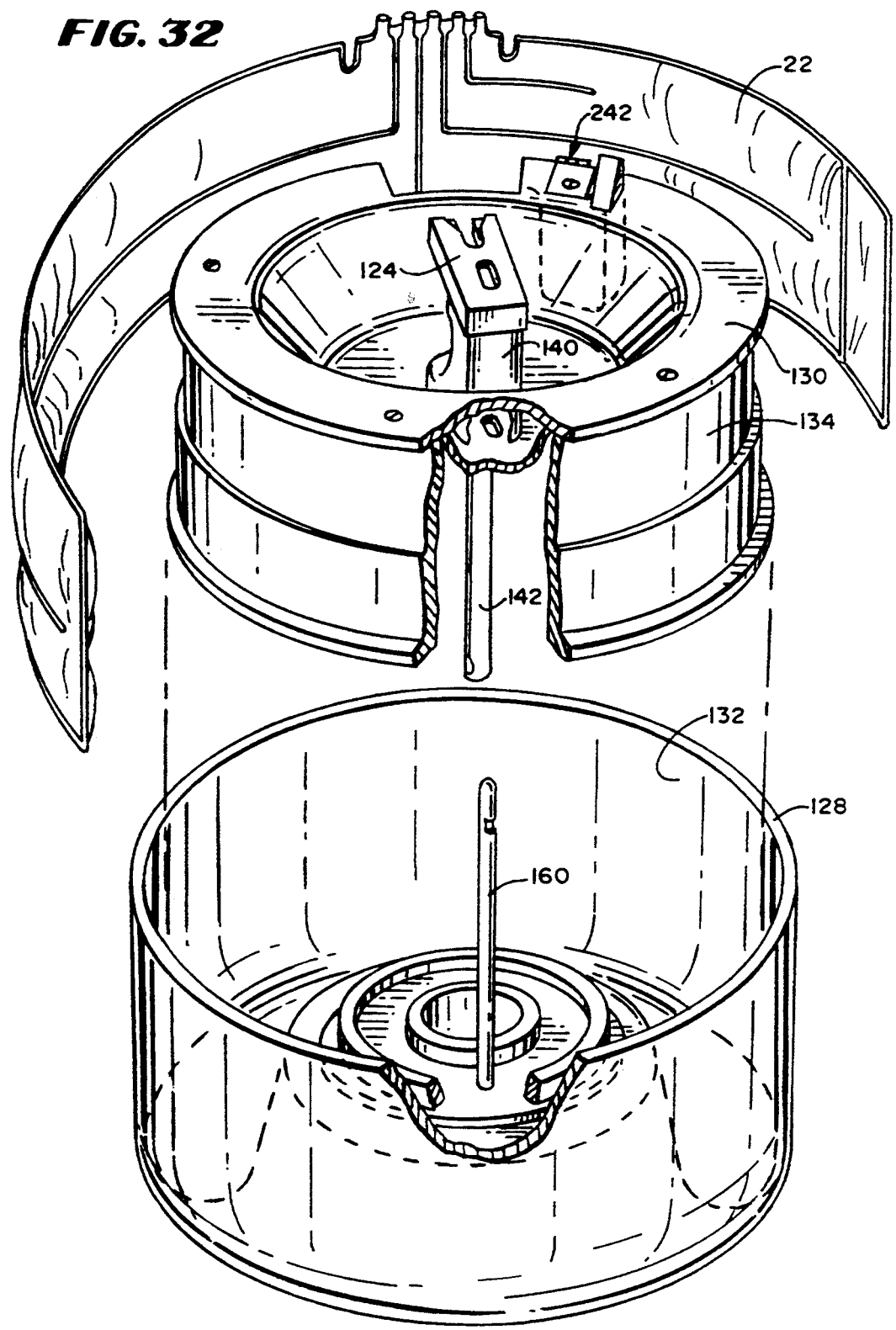
FIG. 32 is an exploded perspective view of an interchangeable centrifuge spool assembly on which a processing chamber can be mounted.

In the embodiment shown in FIG. 32, the interior bowl surface 132 is preformed with a constant outer radius (as measured from the rotational axis). In this arrangement, the exterior spool surface 134 is preformed with contours of varying radii (also as measured from the rotational axis) to present the desired geometry for the low-G region.

Figure 31:
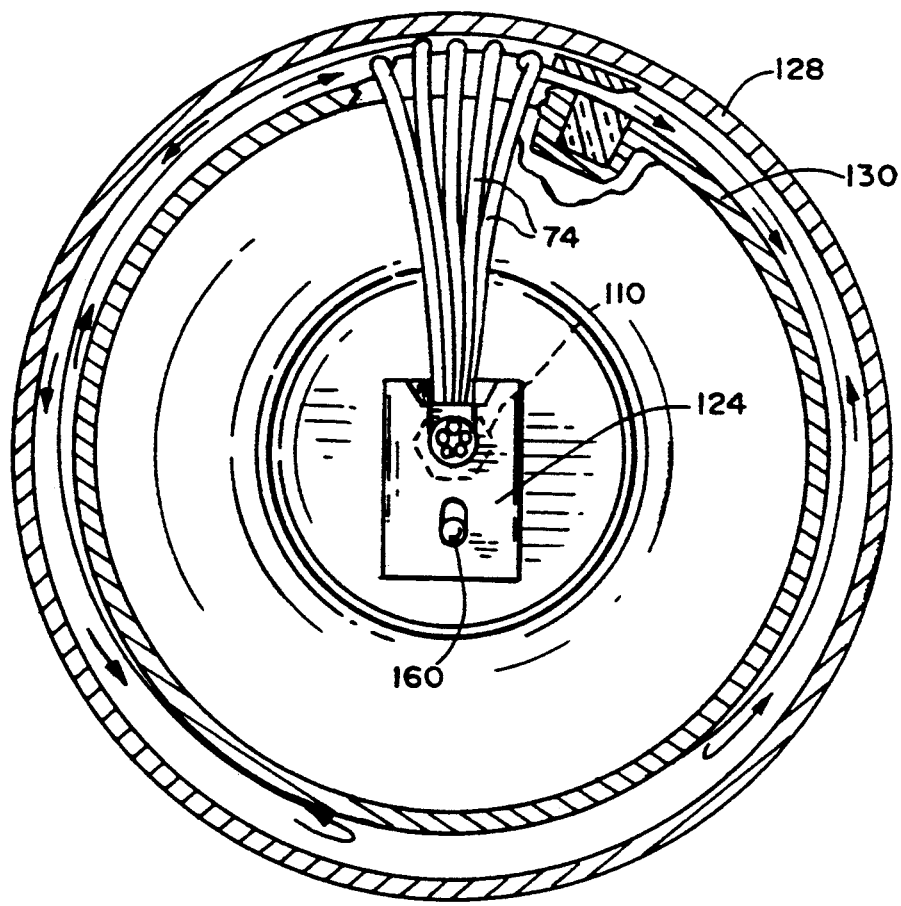
FIG. 31 is a top section view, taken generally along line 31—31 of FIG. 30, of the centrifuge spool holding the processing chamber and in position within the centrifuge bowl for use.

For areas where a non-iso-radial geometry on the high-G wall is desired, the chamber assembly 52 includes an overhanging attachment on the spool 130 extending between the low-G spool surface 134 and the high-G bowl surface 132. In the illustrated embodiment the attachment comprises the hinged flap 242 previously described. As FIG. 31 shows, the flap 242 is clipped, fastened by screws, or otherwise conveniently attached to the spool 130.

In this arrangement, all structures that create the desired contours in both the high-G and low-G regions of the chamber 22 are associated with the inner spool 130. In this way, changes in the contours to do different procedures or air purging methods can be made simply by changing the spool 130.

As FIG. 32 shows, the user can completely separate the spool 130 from the bowl 128 by pulling up on the spool 130 to fully release the spool 130 from the locking pin 160. Since the spool 130 contains the desired contour forming surfaces for the processing chamber 22, the user can easily and quickly remove and exchange a spool having one configuration with a spool having another configuration.

Various features of the invention are set forth in the following claims.

We claim:

1. A processing chamber for a centrifuge comprising a bowl element having an interior wall enclosing an interior area,
a spool element having an exterior surface, and
means connected to the spool element and the bowl element for guiding relative movement between the spool element and the bowl element between a mutually cooperating position, in which the exterior surface of the spool element is located within the interior area of the bowl element to define a processing chamber between the interior bowl wall and the exterior spool surface, and a mutually separated position, in which the exterior surface of the spool element is located at least partially out of the interior area of the bowl element for access.

2. A processing chamber according to claim 1 wherein the spool element includes means exposed when the spool and bowl elements are in their mutually separated position for receiving a processing element upon the spool exterior surface and for retaining the processing element within the processing chamber when the spool and bowl elements are moved to their mutually cooperating position.

3. A processing chamber according to claim 1 and further including means attachable to a drive element for rotating the joined bowl and spool elements about an axis.

4. A processing chamber according to claim 3 wherein the spool element and bowl elements are moved generally along the axis of rotation between their mutually cooperating and mutually separated positions.

5. A processing chamber according to claim 1 and further including means for releasably retaining the spool and bowl elements in their mutually cooperating position.

6. A processing chamber according to claim 1 and further including means for releasably retaining the spool and bowl elements in their mutually separated position.

7. A processing chamber according to claim 1 and further handle means on the spool element for moving the spool element relative to the bowl element between their mutually cooperating and mutually separated positions.

8. A processing chamber according to claim 1 wherein the means that joins the spool and bowl elements allows the spool element to be detached from the bowl element.

9. A processing chamber according to claim 1 wherein the means that joins the spool and bowl elements allows the spool element to be detached from the bowl element for replacement by a second spool element.

10. A processing chamber for a centrifuge comprising a bowl element having an interior wall enclosing an interior area,
a spool element having an exterior surface,
means connected to the spool element and the bowl element for guiding relative movement between the bowl element and the spool element between a mutually cooperating position, in which the exterior surface of the spool element is located within the interior area of the bowl element to define a processing chamber between the interior bowl wall and the exterior spool surface, and a mutually separated position, in which the exterior surface of the spool element is located at least partially out of the interior area of the bowl element for access,
a processing element for receiving fluids for centrifugal separation, and
means for retaining the processing element upon the exterior surface of the spool element within the processing chamber when the spool and bowl elements are in their mutually cooperating position and for releasing the processing element from the exterior surface of the spool element when the spool and bowl elements are in their mutually separated position.

11. A processing chamber according to claim 10 and further including means attachable to a drive element for rotating the joined bowl and spool elements about an axis of rotation.

12. A processing chamber according to claim 11 wherein the spool element and bowl elements are moved generally along the axis of rotation between their mutually cooperating and mutually separated positions.

13. A processing chamber according to claim 10 and further including means for releasably locking the spool and bowl elements in their mutually cooperating position.

14. A processing chamber according to claim 10 or 13 and further including means for releasably locking the spool and bowl elements in their mutually separated position.

15. A processing chamber according to claim 10 and further including handle means on the spool element for moving the spool element relative to the bowl element between their mutually cooperating and mutually separated positions.

16. A processing chamber according to claim 10 wherein the means that joins the spool and bowl elements allows the spool element to be detached from the bowl element.

17. A processing chamber according to claim 10 wherein the means that joins the spool and bowl elements allows the spool element to be detached from the bowl element for replacement by a second spool element.

18. A processing chamber according to claim 10 wherein the processing element includes tubing to convey fluid into and out of the processing element, and
wherein at least one of the spool and bowl elements includes means for holding the tubing.

* * * * *